United States Patent
Milkovisch et al.

(10) Patent No.: US 9,303,509 B2
(45) Date of Patent: Apr. 5, 2016

(54) SINGLE PUMP FOCUSED SAMPLING

(75) Inventors: Mark Milkovisch, Cypress, TX (US); Alexander F. Zazovsky, Houston, TX (US); Simon Ross, Tunbridge Wells (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 662 days.

(21) Appl. No.: 13/522,905

(22) PCT Filed: Jan. 13, 2011

(86) PCT No.: PCT/US2011/021048
§ 371 (c)(1),
(2), (4) Date: Nov. 13, 2012

(87) PCT Pub. No.: WO2011/090868
PCT Pub. Date: Jul. 28, 2011

(65) Prior Publication Data
US 2013/0075088 A1 Mar. 28, 2013

Related U.S. Application Data

(63) Continuation of application No. 12/690,231, filed on Jan. 20, 2010, now Pat. No. 8,210,260.

(51) Int. Cl.
*E21B 49/10* (2006.01)
*E21B 49/08* (2006.01)
(Continued)

(52) U.S. Cl.
CPC .............. *E21B 49/081* (2013.01); *E21B 49/008* (2013.01); *E21B 49/10* (2013.01); *G01N 1/24* (2013.01); *G01N 33/0009* (2013.01)

(58) Field of Classification Search
CPC ....... E21B 19/08; E21B 49/081; E21B 49/10; E21B 49/008
USPC ............................ 166/264, 250.15, 369, 54.1
See application file for complete search history.

(56) References Cited

U.S. PATENT DOCUMENTS 3,121,459 A 2/1964 Van Ness et al.
3,295,615 A 1/1967 Brieger et al.
(Continued)

FOREIGN PATENT DOCUMENTS

GB 2400910 A 10/2004
GB 2417506 A 3/2006
(Continued)

OTHER PUBLICATIONS

Akram, et al., A Model to Predict Wireline Formation Tester Sample Contamination, SPE Annual Technical Conference and Exhibition, Sep. 27-30, 1998, pp. 27-33.
(Continued)

*Primary Examiner* — Brad Harcourt
(74) *Attorney, Agent, or Firm* — Kenneth L. Kincaid

(57) ABSTRACT

An apparatus comprising first and second fluid intakes, a pump, and a sample chamber, may be positioned in a borehole penetrating a subterranean formation. A method of use thereof may comprise drawing fluid from the subterranean formation and into the first and second fluid intakes using the pump, discharging into the borehole at least a portion of the fluid drawn into the second fluid intake, and selectively diverting at least a portion of the fluid drawn into the first fluid intake to the sample chamber.

20 Claims, 21 Drawing Sheets

(51) Int. Cl.
*E21B 49/00* (2006.01)
*G01N 1/24* (2006.01)
*G01N 33/00* (2006.01)

(56) References Cited

U.S. PATENT DOCUMENTS

| | | | |
|---|---|---|---|
| 3,323,361 A | 6/1967 | Lebourg | |
| 3,352,361 A | 11/1967 | Urbanosky | |
| 3,385,364 A | 5/1968 | Whitten | |
| 3,430,181 A | 2/1969 | Urbanosky | |
| 3,430,711 A | 3/1969 | Taggart | |
| 3,530,933 A | 9/1970 | Whitten | |
| 3,565,169 A | 2/1971 | Bell | |
| 3,611,799 A | 10/1971 | Davis | |
| 3,653,436 A | 4/1972 | Anderson et al. | |
| 3,677,081 A | 7/1972 | Newton et al. | |
| 3,782,191 A | 1/1974 | Whitten | |
| 3,813,936 A | 6/1974 | Urbanosky et al. | |
| 3,859,851 A | 1/1975 | Urbanosky | |
| 3,864,970 A | 2/1975 | Bell | |
| 3,924,463 A | 12/1975 | Urbanosky | |
| 3,934,468 A | 1/1976 | Brieger | |
| 3,952,588 A | 4/1976 | Whitten | |
| 4,246,782 A | 1/1981 | Hallmark | |
| 4,287,946 A | 9/1981 | Brieger | |
| 4,339,948 A | 7/1982 | Hallmark | |
| 4,369,654 A | 1/1983 | Hallmark | |
| 4,392,376 A | 7/1983 | Lagus et al. | |
| 4,416,152 A | 11/1983 | Wilson | |
| 4,470,456 A | 9/1984 | Moutray | |
| 4,492,862 A | 1/1985 | Grynberg et al. | |
| 4,513,612 A | 4/1985 | Shalek | |
| 4,535,843 A | 8/1985 | Jageler | |
| 4,573,532 A | 3/1986 | Blake | |
| 4,635,717 A | 1/1987 | Jageler | |
| 4,680,581 A | 7/1987 | Kozlik et al. | |
| 4,690,216 A | 9/1987 | Pritchard | |
| 4,860,581 A | 8/1989 | Zimmerman et al. | |
| 4,879,900 A | 11/1989 | Gilbert | |
| 4,931,343 A | 6/1990 | Becker et al. | |
| 4,936,139 A | 6/1990 | Zimmerman et al. | |
| 4,951,749 A | 8/1990 | Carroll | |
| 4,994,671 A | 2/1991 | Safinya et al. | |
| 5,056,959 A | 10/1991 | Cannac et al. | |
| 5,166,747 A | 11/1992 | Schroeder et al. | |
| 5,230,244 A | 7/1993 | Gilbert | |
| 5,265,015 A | 11/1993 | Auzerais et al. | |
| 5,266,800 A | 11/1993 | Mullins | |
| 5,279,153 A | 1/1994 | Dussan et al. | |
| 5,303,775 A | 4/1994 | Michaels et al. | |
| 5,331,156 A | 7/1994 | Hines et al. | |
| 5,335,542 A | 8/1994 | Ramakrishnan et al. | |
| 5,337,838 A | 8/1994 | Sorensen | |
| 5,377,755 A | 1/1995 | Michaels et al. | |
| 5,517,464 A | 5/1996 | Lerner et al. | |
| 5,540,280 A | 7/1996 | Schultz et al. | |
| 5,587,525 A | 12/1996 | Shwe et al. | |
| 5,622,223 A | 4/1997 | Vasquez | |
| 5,741,962 A | 4/1998 | Birchak et al. | |
| 5,765,637 A | 6/1998 | Dietle et al. | |
| 5,770,798 A | 6/1998 | Georgi et al. | |
| 5,799,733 A | 9/1998 | Ringgenberg et al. | |
| 5,803,186 A | 9/1998 | Berger et al. | |
| 5,826,662 A | 10/1998 | Beck et al. | |
| 5,859,430 A | 1/1999 | Mullins et al. | |
| 5,923,171 A | 7/1999 | Koelman et al. | |
| 5,934,374 A | 8/1999 | Hrametz et al. | |
| 5,939,717 A | 8/1999 | Mullins | |
| 6,157,893 A | 12/2000 | Berger et al. | |
| 6,164,126 A | 12/2000 | Ciglenec et al. | |
| 6,176,323 B1 | 1/2001 | Weirich et al. | |
| 6,178,815 B1 | 1/2001 | Felling et al. | |
| 6,216,662 B1 | 4/2001 | Sapsford | |
| 6,223,822 B1 | 5/2001 | Jones | |
| 6,230,557 B1 | 5/2001 | Ciglenec et al. | |
| 6,274,865 B1 | 8/2001 | Schroer et al. | |
| 6,301,959 B1 | 10/2001 | Hrametz et al. | |
| 6,343,507 B1 | 2/2002 | Felling et al. | |
| 6,350,966 B1 | 2/2002 | Potthof et al. | |
| 6,350,986 B1 | 2/2002 | Mullins et al. | |
| 6,415,864 B1 | 7/2002 | Ramakrishnan et al. | |
| 6,435,279 B1 | 8/2002 | Howe et al. | |
| 6,437,326 B1 | 8/2002 | Yamate et al. | |
| 6,467,544 B1 | 10/2002 | Brown et al. | |
| 6,474,152 B1 | 11/2002 | Mullins et al. | |
| 6,476,384 B1 | 11/2002 | Mullins et al. | |
| 6,478,096 B1 | 11/2002 | Jones et al. | |
| 6,568,487 B2 | 5/2003 | Meister et al. | |
| 6,585,045 B2 | 7/2003 | Lee et al. | |
| 6,609,568 B2 | 8/2003 | Krueger et al. | |
| 6,622,554 B2 | 9/2003 | Manke et al. | |
| 6,627,873 B2 | 9/2003 | Tchakarov et al. | |
| 6,658,930 B2 | 12/2003 | Abbas | |
| 6,659,177 B2 | 12/2003 | Bolze et al. | |
| 6,668,924 B2 | 12/2003 | Bolze et al. | |
| 6,688,390 B2 | 2/2004 | Bolze et al. | |
| 6,707,556 B2 | 3/2004 | Turner et al. | |
| 6,714,872 B2 | 3/2004 | DiFoggio et al. | |
| 6,719,049 B2 | 4/2004 | Sherwood et al. | |
| 6,722,432 B2 | 4/2004 | Spiers et al. | |
| 6,729,399 B2 | 5/2004 | Follini et al. | |
| 6,729,400 B2 | 5/2004 | Mullins et al. | |
| 6,745,835 B2 | 6/2004 | Fields | |
| 6,768,105 B2 | 7/2004 | Mullins et al. | |
| 6,769,296 B2 | 8/2004 | Montalvo et al. | |
| 6,871,713 B2 | 3/2005 | Meister et al. | |
| 6,877,559 B2 | 4/2005 | Hashem | |
| 6,905,241 B2 | 6/2005 | Zazovsky et al. | |
| 6,964,301 B2 | 11/2005 | Hill et al. | |
| 7,031,841 B2 | 4/2006 | Zazovsky et al. | |
| 7,090,012 B2 | 8/2006 | Hill et al. | |
| 7,114,562 B2 | 10/2006 | Fisseler et al. | |
| 7,128,144 B2 | 10/2006 | Fox et al. | |
| 7,178,591 B2 | 2/2007 | Del Campo et al. | |
| 7,234,521 B2 | 6/2007 | Shammai et al. | |
| 7,458,252 B2 | 12/2008 | Freemark et al. | |
| 7,650,937 B2 | 1/2010 | Fox et al. | |
| 2001/0035312 A1 | 11/2001 | Han et al. | |
| 2002/0060067 A1 | 5/2002 | Bolze et al. | |
| 2002/0084072 A1 | 7/2002 | Bolze et al. | |
| 2002/0100585 A1 | 8/2002 | Spiers et al. | |
| 2002/0112854 A1 | 8/2002 | Krueger et al. | |
| 2002/0185313 A1 | 12/2002 | Jones et al. | |
| 2002/0189339 A1 | 12/2002 | Montalvo et al. | |
| 2003/0042021 A1 | 3/2003 | Bolze et al. | |
| 2003/0145652 A1 | 8/2003 | Arian | |
| 2003/0145988 A1 | 8/2003 | Mullins et al. | |
| 2003/0217845 A1 | 11/2003 | Sherwood et al. | |
| 2003/0234120 A1 | 12/2003 | Paluch et al. | |
| 2004/0000433 A1 | 1/2004 | Hill et al. | |
| 2004/0083805 A1 | 5/2004 | Ramakrishnan et al. | |
| 2004/0099443 A1 | 5/2004 | Meister et al. | |
| 2004/0163808 A1 | 8/2004 | Ringgenberg et al. | |
| 2004/0178336 A1 | 9/2004 | DiFoggio | |
| 2004/0231842 A1 | 11/2004 | Shammai et al. | |
| 2005/0039527 A1 | 2/2005 | Dhruva et al. | |
| 2005/0171699 A1 | 8/2005 | Zazovsky et al. | |
| 2005/0182566 A1 | 8/2005 | DiFoggio | |
| 2006/0000603 A1 | 1/2006 | Zazovsky et al. | |
| 2006/0076132 A1 | 4/2006 | Nold et al. | |
| 2006/0117842 A1 | 6/2006 | Ramakrishnan | |
| 2008/0245569 A1 | 10/2008 | Nold et al. | |

FOREIGN PATENT DOCUMENTS

| | | |
|---|---|---|
| GB | 2418938 A | 4/2006 |
| WO | 9630628 A1 | 10/1996 |
| WO | 0050876 A1 | 8/2000 |

(56) References Cited

FOREIGN PATENT DOCUMENTS

| WO | 03098639 A1 | 11/2003 |
|---|---|---|
| WO | 2004020982 A1 | 3/2004 |
| WO | 2005065277 A2 | 7/2005 |

OTHER PUBLICATIONS

Crombie, et al., Innovations in Wireline Fluid Sampling, Oilfield Review, 1998, pp. 26-41.

Dong, et al., In-Situ Contamination Monitoring and GOR Measurement of Formation Fluid Samples, SPE Asia Pacific Oil and Gas Conference and Exhibition, 2002, pp. 1-9.

Hammond, P.S., One or Two Phased Flow During Fluid Sampling by a Wireline Tool, Transport in Porous Media, vol. 6(3), 1991, pp. 299-330.

Hashem, et al., Determination of Producible Hydrocarbon Type and Oil Quality in Wells Drifted with Synthetic Oil-Based Muds, SPE Reservoir Eval. & Eng. 2, Apr. 1999, pp. 125-133.

International Search Report issued in PCT/US2011/021048 on Aug. 5, 2011, 4 pages.

Mullins, at al., Optimization of Wireline Sample Quality by Real-Time Analysis of Oil-Based Mud Contamination, Examples from North Sea Operations, SPE, 2001, pp. 1-16.

Mullins, et al., Real-Time Determination of OBM Filtrate Contamination During Openhole Wireline Sampling, E & P Exchange, Feb. 2001, pp. 24-26.

Schlumberger Wireline & Testing, Schlumberger Wireline Formation Testing & Sampling, 1996, pp. 4-1 through 4-25.

Smits, A.R., In-Situ Optical Fluid Analysis as an Aid to Wireline Formation Sampling, SPE Formation Evaluation, vol. 10(2), Jun. 1995, pp. 91-98.

Written Opinion issued in PCT/US2011/021048 on Aug. 5, 2011, 4 pages.

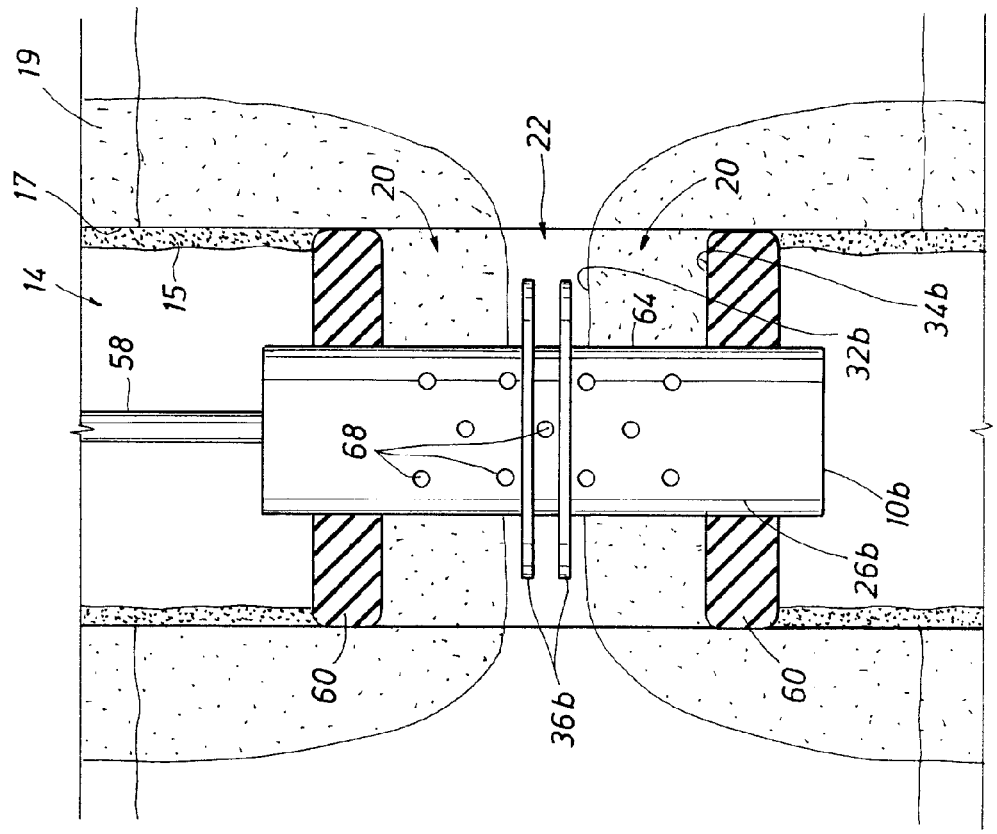
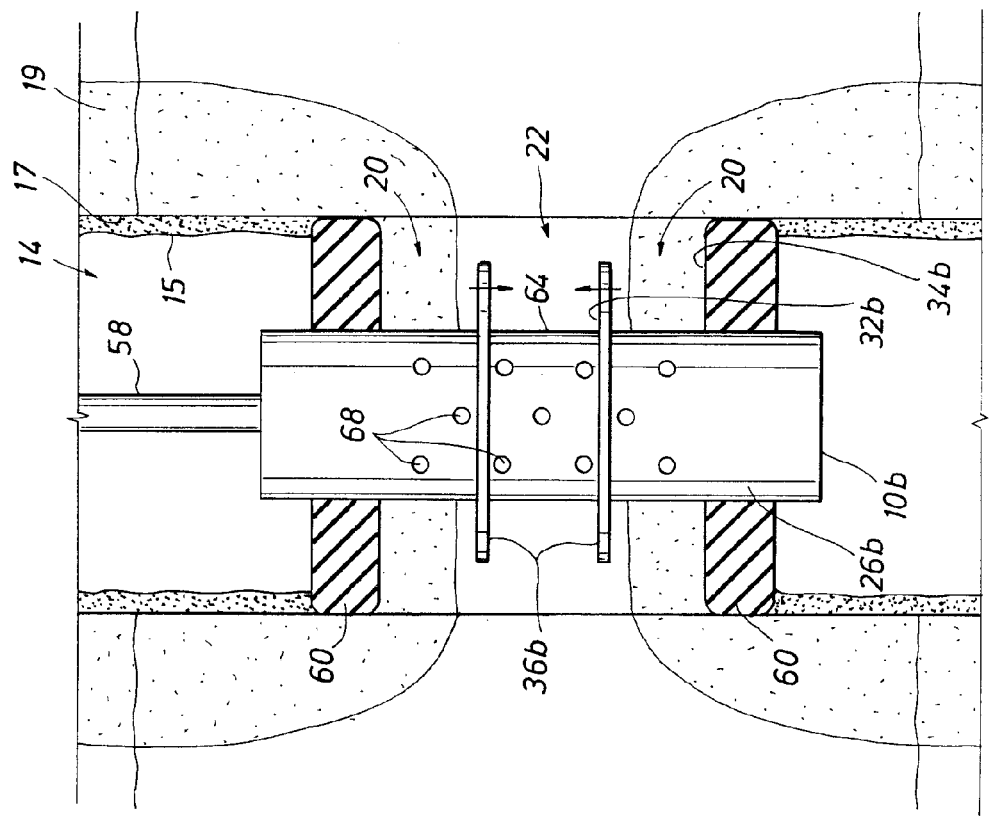

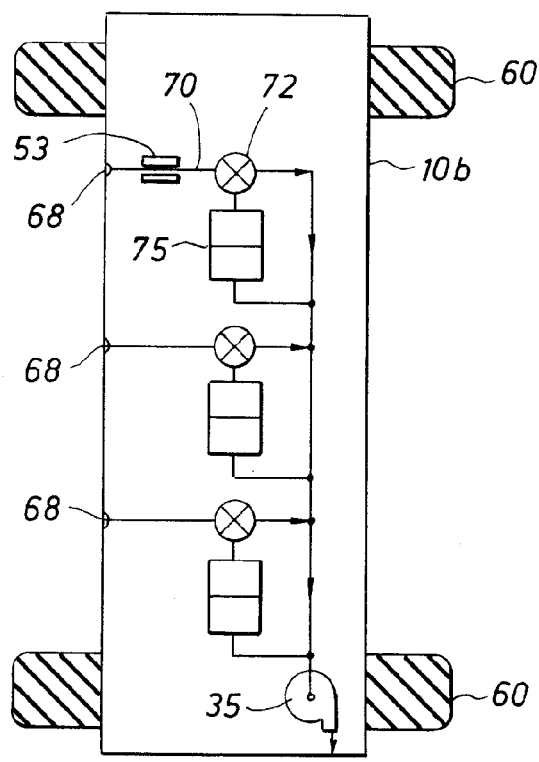
FIG.8C
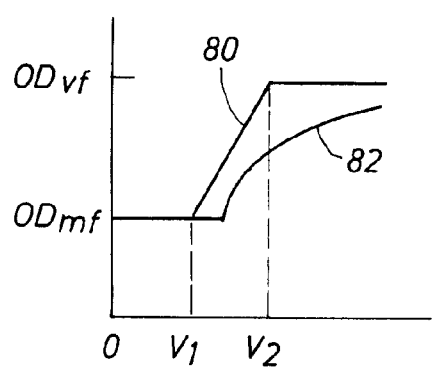
FIG.10
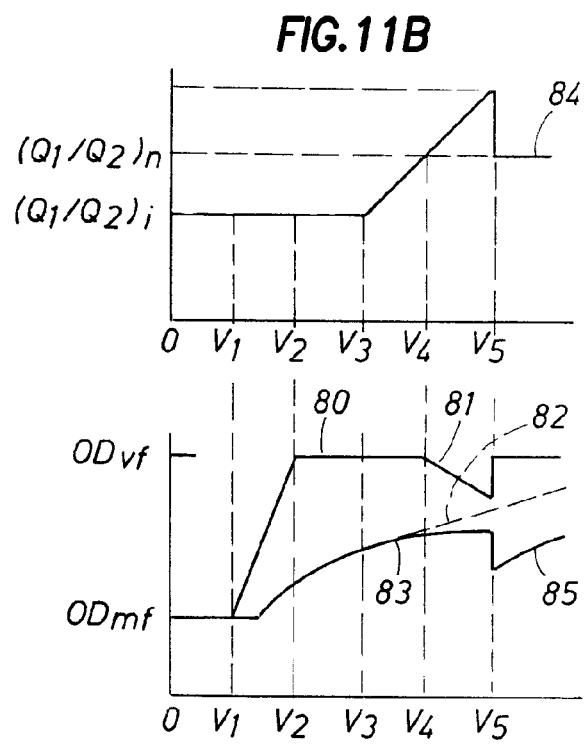
FIG.11B
FIG.11A

SINGLE PUMP FOCUSED SAMPLING

CROSS-REFERENCE TO RELATED APPLICATIONS

This application claims the benefit of U.S. application Ser. No. 12/690,231, entitled "Single Pump Focused Sampling," filed Jan. 20, 2010, the entire disclosure of which is hereby incorporated herein by reference.

BACKGROUND OF THE DISCLOSURE

Wellbores are drilled to locate and produce hydrocarbons. A downhole drilling tool with a bit at an end thereof is advanced into the ground to form a wellbore. As the drilling tool is advanced, a drilling mud is pumped through the drilling tool and out the drill bit to cool the drilling tool and carry away cuttings. The fluid exits the drill bit and flows back up to the surface for recirculation through the tool. The drilling mud is also used to form a mudcake to line the wellbore.

During the drilling operation, it is desirable to perform various evaluations of the formations penetrated by the wellbore. In some cases, the drilling tool may be provided with devices to test and/or sample the surrounding formation. In some cases, the drilling tool may be removed and a wireline tool may be deployed into the wellbore to test and/or sample the formation. In other cases, the drilling tool may be used to perform the testing or sampling. These samples or tests may be used, for example, to locate valuable hydrocarbons. Examples of drilling tools with testing/sampling capabilities are provided in U.S. Pat. Nos. 6,871,713, 7,234,521 and 7,114,562.

Formation evaluation often requires that fluid from the formation be drawn into the downhole tool for testing and/or sampling. Various devices, such as probes, are extended from the downhole tool to establish fluid communication with the formation surrounding the wellbore and to draw fluid into the downhole tool. A typical probe is a circular element extended from the downhole tool and positioned against the sidewall of the wellbore. A rubber packer at the end of the probe is used to create a seal with the wellbore sidewall. Another device used to form a seal with the wellbore sidewall is referred to as a dual packer. With a dual packer, two elastomeric rings expand radially about the tool to isolate a portion of the wellbore therebetween. The rings form a seal with the wellbore wall and permit fluid to be drawn into the isolated portion of the wellbore and into an inlet in the downhole tool.

The mudcake lining the wellbore is often useful in assisting the probe and/or dual packers in making the seal with the wellbore wall. Once the seal is made, fluid from the formation is drawn into the downhole tool through an inlet by lowering the pressure in the downhole tool. Examples of probes and/or packers used in downhole tools are described in U.S. Pat. Nos. 6,301,959; 4,860,581; 4,936,139; 6,585,045; 6,609,568; 6,719,049 and 6,964,301.

The collection and sampling of underground fluids contained in subsurface formations is well known. In the petroleum exploration and recovery industries, for example, samples of formation fluids are collected and analyzed for various purposes, such as to determine the existence, composition and/or producibility of subsurface hydrocarbon fluid reservoirs. This aspect of the exploration and recovery process can be crucial in developing drilling strategies, and can impact significant financial expenditures and/or savings.

To conduct valid fluid analysis, the fluid obtained from the subsurface formation should possess sufficient purity, or be virgin fluid, to adequately represent the fluid contained in the formation. As used within the scope of the present disclosure, the terms "virgin fluid," "acceptable virgin fluid" and variations thereof mean subsurface fluid that is pure, pristine, connate, uncontaminated or otherwise considered in the fluid sampling and analysis field to be sufficiently or acceptably representative of a given formation for valid hydrocarbon sampling and/or evaluation.

Various challenges may arise in the process of obtaining virgin fluid from subsurface formations. Again with reference to the petroleum-related industries, for example, the earth around the borehole from which fluid samples are sought typically contains contaminates, such as filtrate from the mud utilized in drilling the borehole. This material often contaminates the virgin fluid as it passes through the borehole, resulting in fluid that is generally unacceptable for hydrocarbon fluid sampling and/or evaluation. Such fluid is referred to herein as "contaminated fluid." Because fluid is sampled through the borehole, mudcake, cement and/or other layers, it is difficult to avoid contamination of the fluid sample as it flows from the formation and into a downhole tool during sampling. A challenge thus lies in minimizing the contamination of the virgin fluid during fluid extraction from the formation.

FIG. 1 depicts a subsurface formation 16 penetrated by a wellbore 14. A layer of mud cake 15 lines a sidewall 17 of the wellbore 14. Due to invasion of mud filtrate into the formation during drilling, the wellbore is surrounded by a cylindrical layer known as the invaded zone 19 containing contaminated fluid 20 that may or may not be mixed with virgin fluid. Beyond the sidewall of the wellbore and surrounding contaminated fluid, virgin fluid 22 is located in the formation 16. As shown in FIG. 1, contaminates tend to be located near the wellbore wall in the invaded zone 19.

FIG. 2 shows the typical flow patterns of the formation fluid as it passes from subsurface formation 16 into a downhole tool 1. The downhole tool 1 is positioned adjacent the formation and a probe 2 is extended from the downhole tool through the mudcake 15 to the sidewall 17 of the wellbore 14. The probe 2 is placed in fluid communication with the formation 16 so that formation fluid may be passed into the downhole tool 1. Initially, as shown in FIG. 1, the invaded zone 19 surrounds the sidewall 17 and contains contamination. As fluid initially passes into the probe 2, the contaminated fluid 20 from the invaded zone 19 is drawn into the probe with the fluid thereby generating fluid unsuitable for sampling. However, as shown in FIG. 2, after a certain amount of fluid passes through the probe 2, the virgin fluid 22 breaks through and begins entering the probe. In other words, a more central portion of the fluid flowing into the probe gives way to the virgin fluid, while the remaining portion of the fluid is contaminated fluid from the invasion zone. The challenge remains in adapting to the flow of the fluid so that the virgin fluid is collected in the downhole tool during sampling.

Formation evaluation is typically performed on fluids drawn into the downhole tool. Techniques currently exist for performing various measurements, pretests and/or sample collection of fluids that enter the downhole tool. Various methods and devices have been proposed for obtaining subsurface fluids for sampling and evaluation. For example, U.S. Pat. Nos. 6,230,557, 6,223,822, 4,416,152, and 3,611,799, and PCT Patent Application Publication No. WO 96/30628, describe certain probes and related techniques to improve sampling. However, it has been discovered that when the formation fluid passes into the downhole tool, various contaminants, such as wellbore fluids and/or drilling mud, may enter the tool with the formation fluids. These contaminates may affect the quality of measurements and/or samples of the formation fluids. Moreover, contamination may cause costly delays in the wellbore operations by requiring additional time for more testing and/or sampling. Additionally, such problems may yield false results that are erroneous and/or unusable. Other techniques have been developed to separate virgin fluids during sampling. For example, U.S. Pat. No. 6,301,959 discloses a sampling probe with two hydraulic lines to recover formation fluids from two zones in the borehole. In this patent, borehole fluids are drawn into a guard zone separate from fluids drawn into a probe zone. Despite such advances in sampling, there remains a need to develop techniques for fluid sampling to optimize the quality of the sample and efficiency of the sampling process.

To increase sample quality, it is desirable that the formation fluid entering into the downhole tool be sufficiently "clean" or "virgin" for valid testing. In other words, the formation fluid should have little or no contamination. Attempts have been made to eliminate contaminates from entering the downhole tool with the formation fluid. For example, as depicted in U.S. Pat. No. 4,951,749, filters have been positioned in probes to block contaminates from entering the downhole tool with the formation fluid. Additionally, as shown in U.S. Pat. No. 6,301,959, a probe is provided with a guard ring to divert contaminated fluids away from clean fluid as it enters the probe.

Techniques have also been developed to evaluate fluid passing through the tool to determine contamination levels. In some cases, techniques and mathematical models have been developed for predicting contamination for a merged flowline. See, for example, PCT Patent Application No. WO 2005065277 and PCT Patent Application No. 00/50876, the entire contents of which are hereby incorporated by reference. Techniques for predicting contamination levels and determining cleanup times are described in P. S. Hammond, "One or Two Phased Flow During fluid Sampling by a Wireline Tool," Transport in Porous Media, Vol. 6, p. 299-330 (1991), the entire contents of which are hereby incorporated by reference. Hammond describes a semi-empirical technique for estimating contamination levels and cleanup time of fluid passing into a downhole tool through a single flowline.

Despite the existence of techniques for performing formation evaluation and for attempting to deal with contamination, there remains a need to manipulate the flow of fluids through the downhole tool to reduce contamination as it enters and/or passed through the downhole tool. It is desirable that such techniques are capable of diverting contaminants away from clean fluid. Techniques have also been developed for contamination monitoring. However, such techniques relate to single flowline applications. It is desirable to provide contamination monitoring techniques applicable to multi-flowline operations.

It is further desirable that techniques be capable of one of more of the following, among others: analyzing the fluid passing through the flowlines, selectively manipulating the flow of fluid through the downhole tool, responding to detected contamination, removing contamination, providing flexibility in handling fluids in the downhole tool, selectively collecting virgin fluid apart from contaminated fluid; separating virgin fluid from contaminated fluid; optimizing the quantity and/or quality of virgin fluid extracted from the formation for sampling; adjusting the flow of fluid according to the sampling needs; controlling the sampling operation manually and/or automatically and/or on a real-time basis, analyzing the fluid flow to detect contamination levels, estimating time to clean up contamination, calibrating flowline measurements, cross-checking flowline measurements, selectively combining and/or separating flowlines, determining contamination levels, and comparing flowline data to known values. Finally, it is desirable that techniques be developed to adjust the wellbore operation to optimize the testing and/or sampling process. In some cases, such optimization may be in response to real time measurements, operator commands, pre-programmed instructions and/or other inputs. To this end, aspects of the present disclosure are directed towards optimizing the formation evaluation process.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 8A is a schematic view of an alternate embodiment of the downhole tool and fluid flowing system having dual packers and walls;

FIG. 8B is a schematic view of the downhole tool of FIG. 8A with the walls moved together in response to changes in the fluid flow;

FIG. 8C is a schematic view of the flow section of the downhole tool of FIG. 8A;

FIG. 10 is a graphical depiction of the optical density signatures of fluid entering the probe at a given volume;

FIG. 11A is a graphical depiction of optical density signatures of FIG. 10 deviated during sampling at a given volume;

FIG. 11B is a graphical depiction of the ratio of flow rates corresponding to the given volume for the optical densities of FIG. 11A;

DETAILED DESCRIPTION

Figure 1:
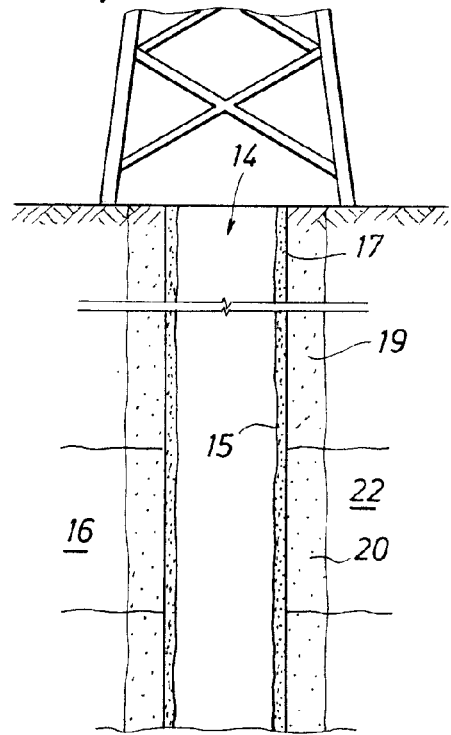
FIG. 1 is a schematic view of a subsurface formation penetrated by a wellbore lined with mudcake, depicting the virgin fluid in the subsurface formation.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 3:
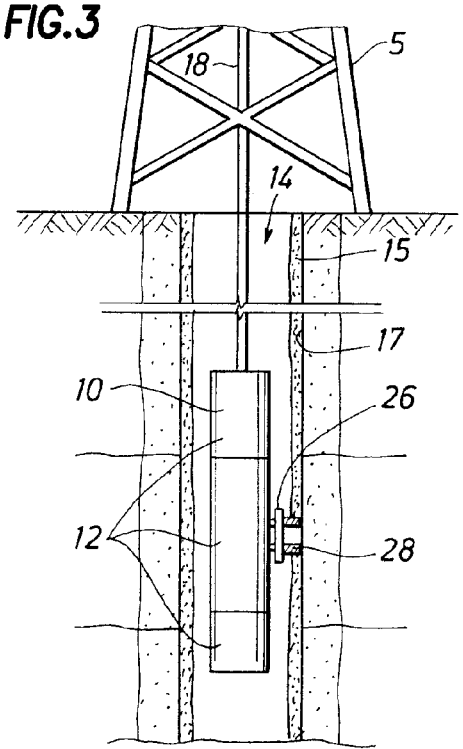
FIG. 3 is a schematic view of down hole wireline tool having a fluid sampling device.

Referring to FIG. 3, an example environment with which aspects of the present disclosure may be used is shown. In the illustrated example, provided is a down hole tool 10, such as a Modular Formation Dynamics Tester (MDT) by Schlumberger Corporation, and further depicted, for example, in U.S. Pat. Nos. 4,936,139 and 4,860,581, which are hereby incorporated by reference herein in their entireties. The downhole tool 10 is deployable into bore hole 14 and suspended therein with a conventional wire line 18, or conductor or conventional tubing or coiled tubing, below a rig 5 as will be appreciated by one of skill in the art. The illustrated tool 10 is provided with various modules and/or components 12, including, but not limited to, a fluid sampling device 26 used to obtain fluid samples from the subsurface formation 16. The fluid sampling device 26 is provided with a probe 28 extendable through the mudcake 15 and to sidewall 17 of the borehole 14 for collecting samples. The samples are drawn into the downhole tool 10 through the probe 28.

Figure 4:
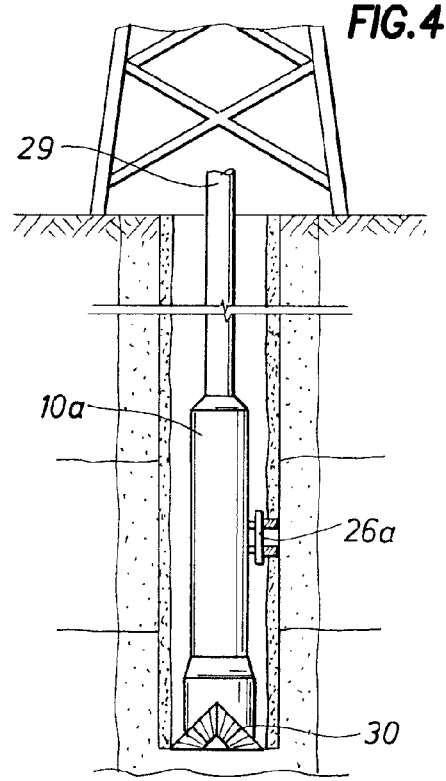
FIG. 4 is a schematic view of a downhole drilling tool with an alternate embodiment of the fluid sampling device of FIG. 3.

While FIG. 3 depicts a modular wireline sampling tool for collecting samples according to one or more aspects of the present disclosure, it will be appreciated by one of skill in the art that such system may be used in any downhole tool. For example, FIG. 4 shows an alternate downhole tool 10a having a fluid sampling system 26a therein. In this example, the downhole tool 10a is a drilling tool including a drill string 29 and a drill bit 30. The downhole drilling tool 10a may be of a variety of drilling tools, such as a Measurement-While-Drilling (MWD), Logging-While Drilling (LWD) or other drilling system. The tools 10 and 10a of FIGS. 3 and 4, respectively, may have alternate configurations, such as modular, unitary, wireline, coiled tubing, autonomous, drilling and other variations of downhole tools.

Figure 5:
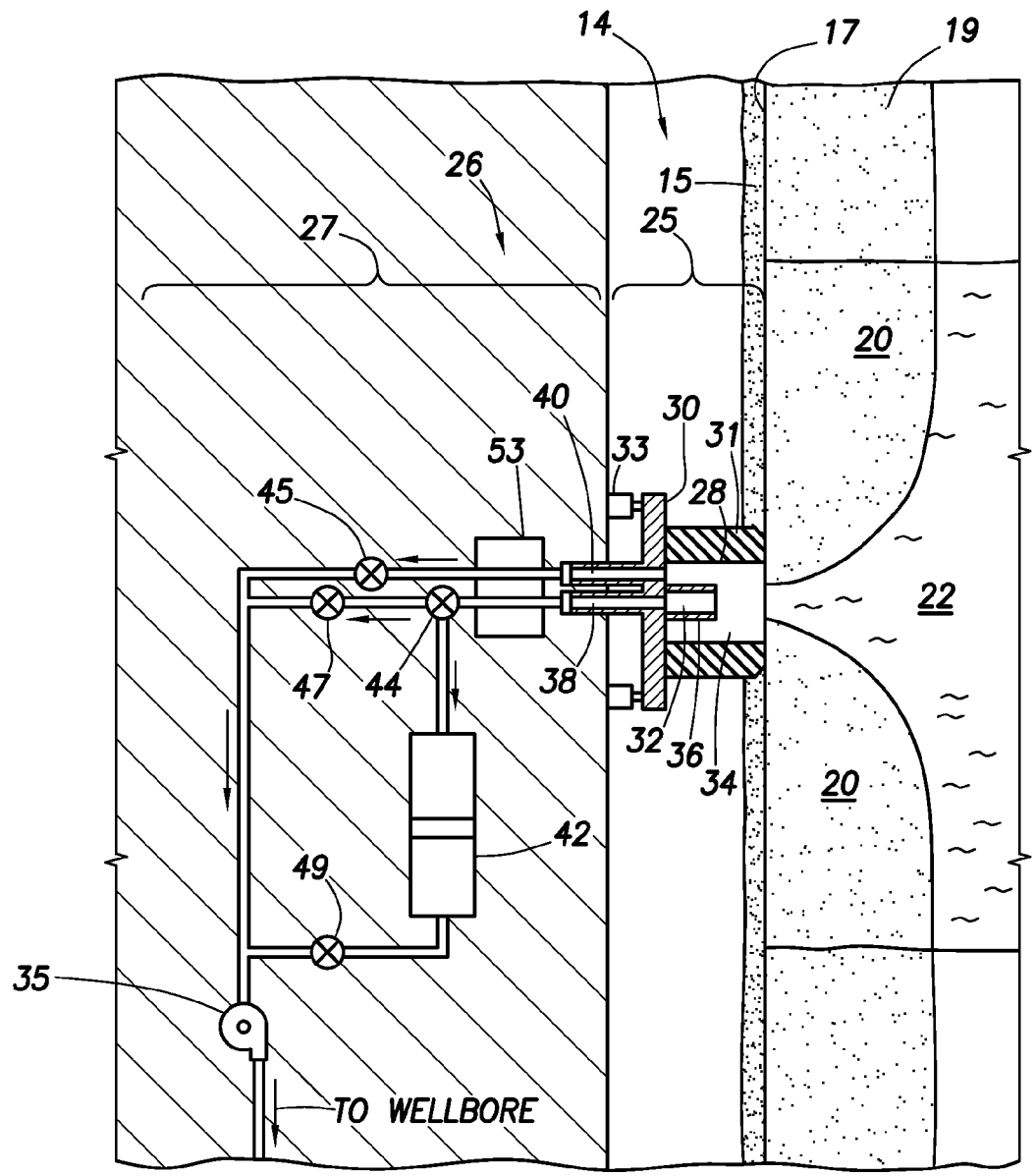
FIG. 5 is a detailed view of the fluid sampling device of FIG. 3 depicting an intake section and a fluid flow section.

Referring now to FIG. 5, the fluid sampling system 26 of FIG. 3 is shown in greater detail. The sampling system 26 includes an intake section 25 and a flow section 27 for selectively drawing fluid into the desired portion of the downhole tool.

The intake section 25 includes a probe 28 mounted on an extendable base 30 having a seal 31, such as a packer, for sealingly engaging the borehole wall 17 around the probe 28. The intake section 25 is selectively extendable from the downhole tool 10 via extension pistons 33. The probe 28 is provided with an interior channel 32 and an exterior channel 34 separated by wall 36. The wall 36 is preferably concentric with the probe 28. However, the geometry of the probe and the corresponding wall may be of any geometry. Additionally, one or more walls 36 may be used in various configurations within the probe.

The flow section 27 includes flow lines 38 and 40 driven by one or more pumps 35. A first flow line 38 is in fluid communication with the interior channel 32, and a second flow line 40 is in fluid communication with the exterior channel 34. The illustrated flow section may include one or more flow control devices, such as the pump 35 and valves 44, 45, 47 and 49 depicted in FIG. 5, for selectively drawing fluid into various portions of the flow section 27. Fluid is drawn from the formation through the interior and exterior channels and into their corresponding flow lines.

Preferably, contaminated fluid may be passed from the formation through exterior channel 34, into flow line 40 and discharged into the wellbore 14. Preferably, fluid passes from the formation into the interior channel 32, through flow line 38 and either diverted into one or more sample chambers 42, or discharged into the wellbore. Once it is determined that the fluid passing into flow line 38 is virgin fluid, a valve 44 and/or 49 may be activated using known control techniques by manual and/or automatic operation to divert fluid into the sample chamber.

The fluid sampling system 26 is also preferably provided with one or more fluid monitoring systems 53 for analyzing the fluid as it enters the probe 28. The fluid monitoring system 53 may be provided with various monitoring devices, such as optical fluid analyzers, as will be discussed more fully herein.

The details of the various arrangements and components of the fluid sampling system 26 described above as well as alternate arrangements and components for the system 26 would be known to persons skilled in the art and found in various other patents and printed publications, such as those discussed herein. Moreover, the particular arrangement and components of the downhole fluid sampling system 26 may vary depending upon factors in each particular design, use or situation. Thus, neither the system 26 nor the present disclosure are limited to the above described arrangements and components and may include any suitable components and arrangement. For example, various flow lines, pump placement and valving may be adjusted to provide for a variety of configurations. Similarly, the arrangement and components of the downhole tool 10 may vary depending upon factors in each particular design, or use, situation. The above description of exemplary components and environments of the tool 10 with which the fluid sampling device 26 of the present disclosure may be used is provided for illustrative purposes only and is not limiting upon the present disclosure.

With continuing reference to FIG. 5, the flow pattern of fluid passing into the downhole tool 10 is illustrated. Initially, as shown in FIG. 1, an invaded zone 19 surrounds the borehole wall 17. Virgin fluid 22 is located in the formation 16 behind the invaded zone 19. At some time during the process, as fluid is extracted from the formation 16 into the probe 28, virgin fluid breaks through and enters the probe 28 as shown in FIG. 5. As the fluid flows into the probe, the contaminated fluid 22 in the invaded zone 19 near the interior channel 32 is eventually removed and gives way to the virgin fluid 22. Thus, only virgin fluid 22 is drawn into the interior channel 32, while the contaminated fluid 20 flows into the exterior channel 34 of the probe 28. To enable such result, the flow patterns, pressures and dimensions of the probe may be altered to achieve the desired flow path as will be described more fully herein.

Figure 6A:
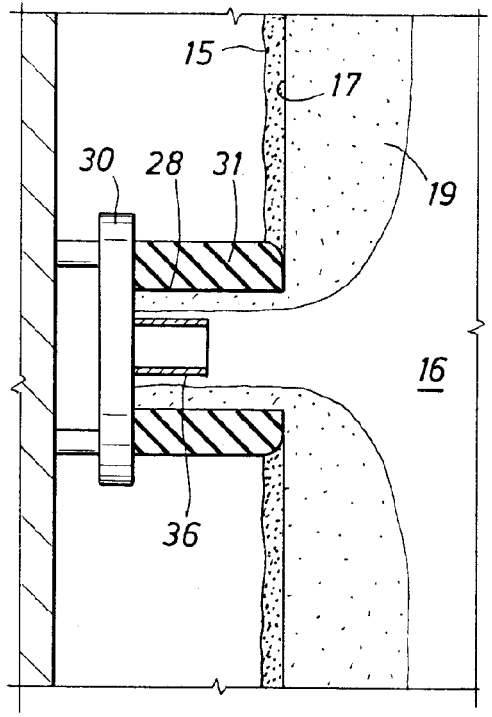
FIG. 6A is a detailed view of the intake section of FIG. 5 depicting the flow of fluid into a probe having a wall defining an interior channel, the wall recessed within the probe.

Referring now to FIGS. 6A-6J, various embodiments of the probe 28 are shown in greater detail. In FIG. 6A, the base 30 is shown supporting the seal 31 in sealing engagement with the borehole wall 17. The probe 28 preferably extends beyond the seal 31 and penetrates the mudcake 15. The probe 28 is placed in fluid communication with the formation 16.

The wall 36 is preferably recessed a distance within the probe 28. In this configuration, pressure along the formation wall is automatically equalized in the interior and exterior channels. The probe 28 and the wall 36 are preferably concentric circles, but may be of alternate geometries depending on the application or needs of the operation. Additional walls, channels and/or flow lines may be incorporated in various configurations to further optimize sampling.

Figure 6B:
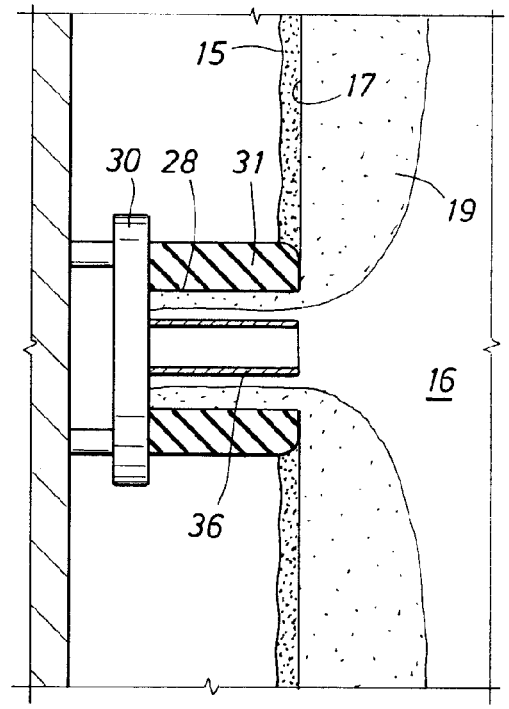
FIG. 6B is an alternate embodiment of the probe of FIG. 6A having a wall defining an interior channel, the wall flush with the probe.

The wall 36 is preferably adjustable to optimize the flow of virgin fluid into the probe. Because of varying flow conditions, it is desirable to adjust the position of the wall 36 so that the maximum amount of virgin fluid may be collected with the greatest efficiency. For example, the wall 36 may be moved or adjusted to various depths relative to the probe 28. As shown in FIG. 6B, the wall 36 may be positioned flush with the probe. In this configuration, the pressure in the interior channel along the formation may be different from the pressure in the exterior channel along the formation.

Figure 6C:
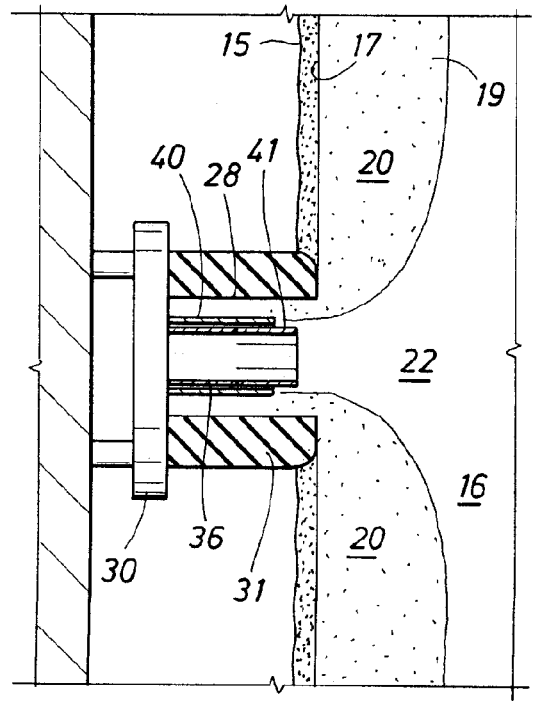
FIG. 6C is an alternate embodiment of the probe of FIG. 6A having a sizer capable of reducing the size of the interior channel.
Figure 6D:
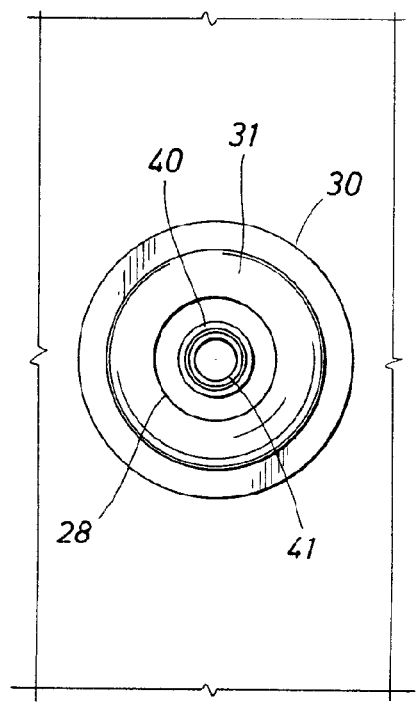
FIG. 6D is a cross-sectional view of the probe of FIG. 6C.
Figure 6E:
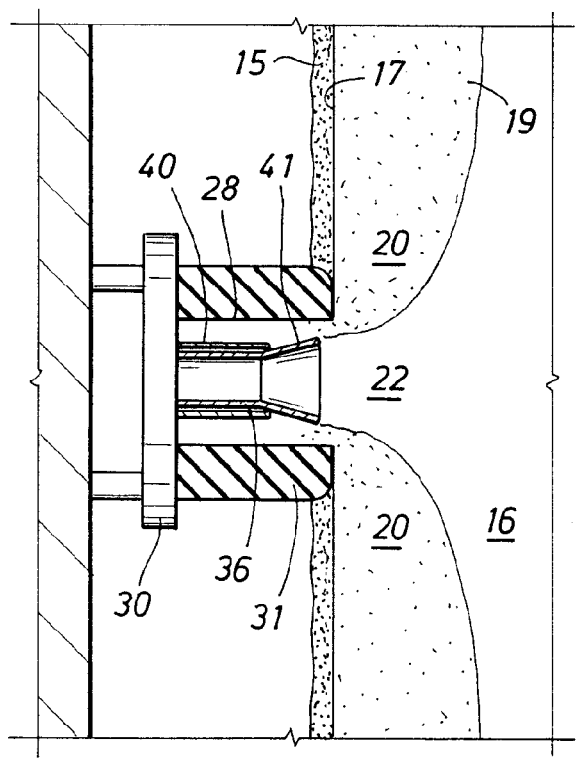
FIG. 6E is an alternate embodiment of the probe of FIG. 6A having a sizer capable of increasing the size of the interior channel.
Figure 6F:
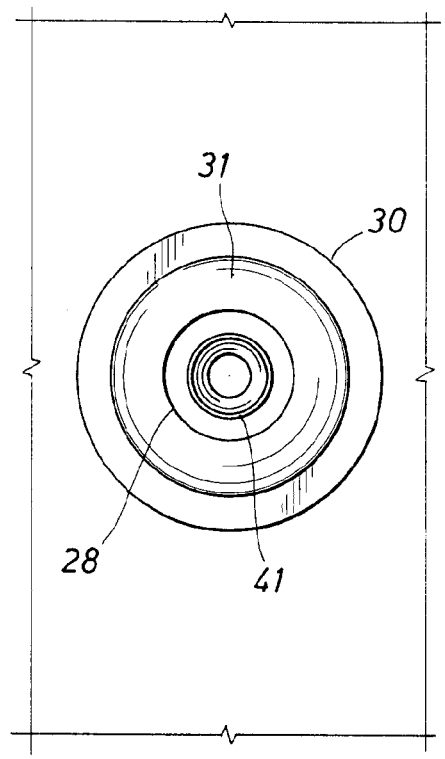
FIG. 6F is a cross-sectional view of the probe of FIG. 6E.

Referring now to FIGS. 6C-6H, the wall 36 is preferably capable of varying the size and/or orientation of the interior channel 32. As shown in FIG. 6C through 6F, the diameter of a portion or all of the wall 36 is preferably adjustable to align with the flow of contaminated fluid 20 from the invaded zone 19 and/or the virgin fluid 22 from the formation 16 into the probe 28. The wall 36 may be provided with a mouthpiece 41 and a guide 40 adapted to allow selective modification of the size and/or dimension of the interior channel. The mouthpiece 41 is selectively movable between an expanded and a collapsed position by moving the guide 40 along the wall 36. In FIGS. 6C and 6D, the guide 40 is surrounds the mouthpiece 41 and maintains it in the collapsed position to reduce the size of the interior flow channel in response to a narrower flow of virgin fluid 22. In FIGS. 6E and 6F, the guide 41 is retracted so that the mouthpiece 41 is expanded to increase the size of the interior flow channel in response to a wider flow of virgin fluid 22.

The mouthpiece depicted in FIGS. 6C-6F may be a folded metal spring, a cylindrical bellows, a metal energized elastomer, a seal, or any other device capable of functioning to selectively expand or extend the wall as desired. Other devices capable of expanding the cross-sectional area of the wall 36 may be envisioned. For example, an expandable spring cylinder pinned at one end may also be used.

Figure 6G:
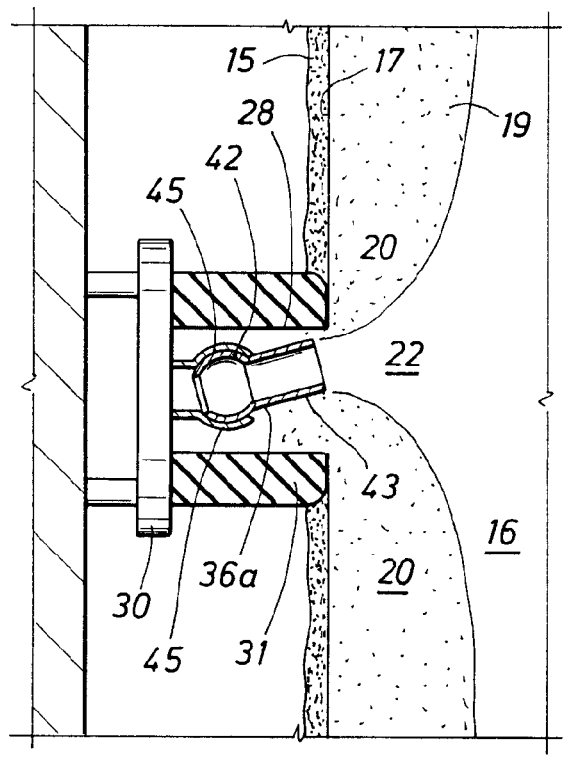
FIG. 6G is an alternate embodiment of the probe of FIG. 6A having a pivoter that adjusts the position of the interior channel within the probe.
Figure 6H:
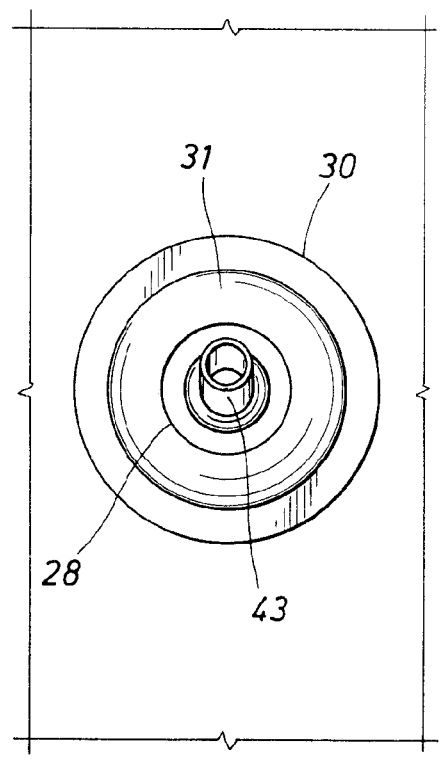
FIG. 6H is a cross-sectional view of the probe of FIG. 6G.

As shown in FIGS. 6G and 6H, the probe 28 may also be provided with a wall 36a having a first portion 42, a second portion 43 and a seal bearing 45 therebetween to allow selective adjustment of the orientation of the wall 36a within the probe. The second portion 43 is desirably movable within the probe 28 to locate an optimal alignment with the flow of virgin fluid 20.

Figure 6I:
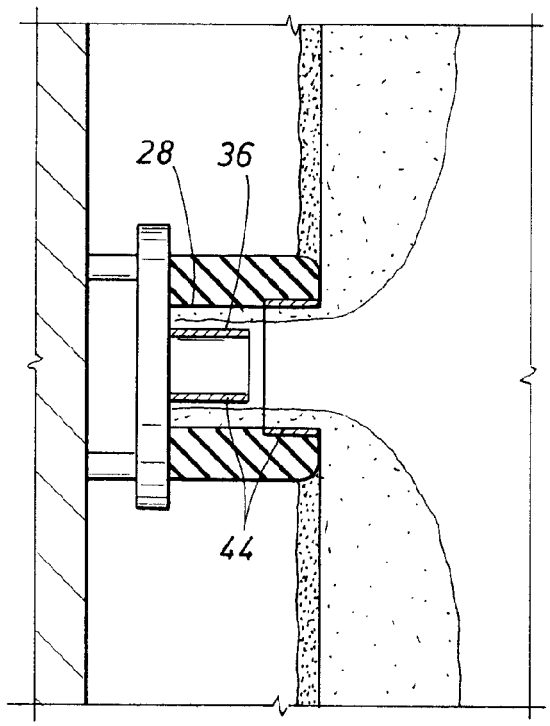
FIG. 6I is an alternate embodiment of the probe of FIG. 6A having a shaper that adjusts the shape of the probe and/or interior channel.
Figure 6J:
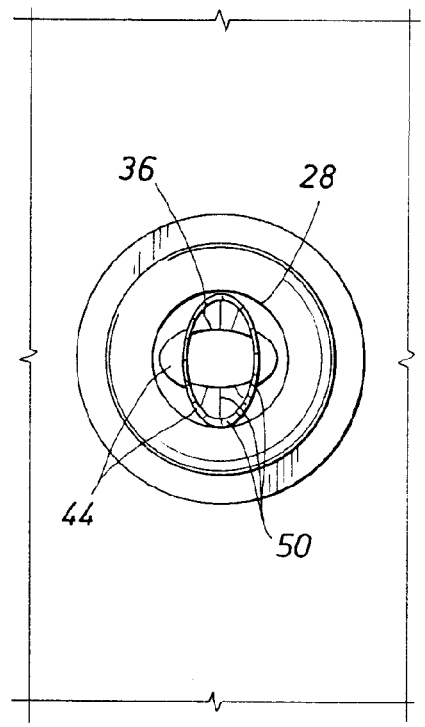
FIG. 6J is a cross-sectional view of the probe of FIG. 6I.

Additionally, as shown in FIGS. 6I and 6J, one or more shapers 44 may also be provided to conform the probe 28 and/or wall 36 into a desired shape. The shapers 44 have two more fingers 50 adapted to apply force to various positions about the probe and/or wall 36 causing the shape to deform. When the probe 40 and or wall 36 are extended as depicted in FIG. 6E, the shaper 44 may be extended about at least a portion of the mouthpiece 41 to selectively deform the mouthpiece to the desired shape. If desired, the shapers apply pressure to various positions around the probe and/or wall to generate the desired shape.

The sizer, pivoter and/or shaper may be any electronic mechanism capable of selectively moving the wall 36 as provided herein. One or more devices may be used to perform one or more of the adjustments. Such devices may include a selectively controllable slidable collar, a pleated tube, or cylindrical bellows or spring, an elastomeric ring with embedded spring-biased metal fingers, a flared elastomeric tube, a spring cylinder, and/or any suitable components with any suitable capabilities and operation may be used to provide any desired variability.

These and other adjustment devices may be used to alter the channels for fluid flow. Thus, a variety of configurations may be generated by combining one or more of the adjustable features.

Figure 7A:
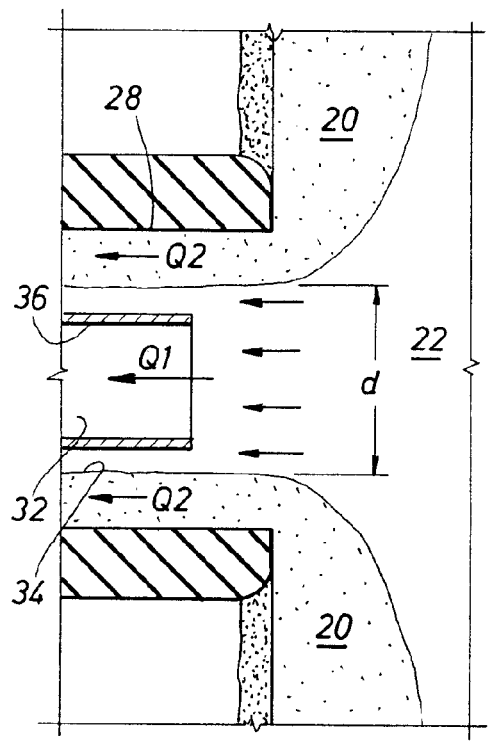
FIG. 7A is a schematic view of the probe of FIG. 6A with the flow of fluid from the formation into the probe with the pressure and/or flow rate balanced between the interior and exterior flow channels for substantially linear flow into the probe.
Figure 7B:
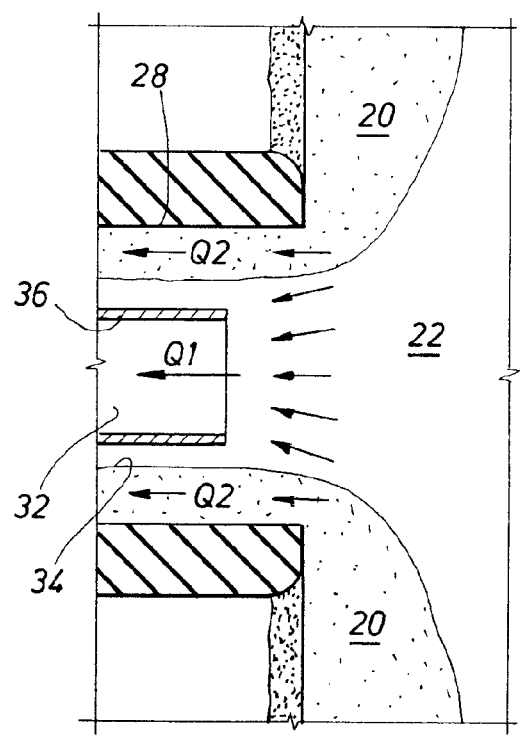
FIG. 7B is a schematic view of the probe of FIG. 7A with the flow rate of the interior channel greater than the flow rate of the exterior channel.

Now referring to FIGS. 7A and 7B, the flow characteristics are shown in greater detail. Various flow characteristics of the probe 28 may be adjusted. For example, as shown in FIG. 7A, the probe 28 may be designed to allow controlled flow separation of virgin fluid 22 into the interior channel 32 and contaminated fluid 20 into the exterior channel 34. This may be desirable, for example, to assist in minimizing the sampling time required before acceptable virgin fluid is flowing into the interior channel 32 and/or to optimize or increase the quantity of virgin fluid flowing into the interior channel 32, or other reasons.

The ratio of fluid flow rates within the interior channel 32 and the exterior channel 34 may be varied to optimize, or increase, the volume of virgin fluid drawn into the interior channel 32 as the amount of contaminated fluid 20 and/or virgin fluid 22 changes over time. The diameter d of the area of virgin fluid flowing into the probe may increase or decrease depending on wellbore and/or formation conditions. Where the diameter d expands, it is desirable to increase the amount of flow into the interior channel. This may be done by altering the wall 36 as previously described. Alternatively or simultaneously, the flow rates to the respective channels may be altered to further increase the flow of virgin fluid into the interior channel.

The comparative flow rate into the channels 32 and 34 of the probe 28 may be represented by a ratio of flow rates $Q_1/Q_2$. The flow rate into the interior channel 32 is represented by $Q_1$ and the flow rate in the exterior channel 34 is represented by $Q_2$. The flow rate $Q_1$ in the interior channel 32 may be selectively increased and/or the flow rate $Q_2$ in the exterior channel 34 may be decreased to allow more fluid to be drawn into the interior channel 32. Alternatively, the flow rate $Q_1$ in the interior channel 32 may be selectively decreased and/or the flow rate ($Q_2$) in the exterior channel 34 may be increased to allow less fluid to be drawn into the interior channel 32.

As shown in FIG. 7A, $Q_1$ and $Q_2$ represent the flow of fluid through the probe 28. The flow of fluid into the interior channel 32 may be altered by increasing or decreasing the flow rate to the interior channel 32 and/or the exterior channel 34. For example, as shown in FIG. 7B, the flow of fluid into the interior channel 32 may be increased by increasing the flow rate $Q_1$ through the interior channel 32, and/or by decreasing the flow rate $Q_2$ through the exterior channel 34. As indicated by the arrows, the change in the ratio $Q_1/Q_2$ steers a greater amount of the fluid into the interior channel 32 and increases the amount of virgin fluid drawn into the downhole tool (FIG. 5).

The flow rates within the channels 32 and 34 may be selectively controllable in any desirable manner and with any suitable component(s). For example, one or more flow control device 35 is in fluid communication with each flowline 38, 40 may be activated to adjust the flow of fluid into the respective channels (FIG. 5). The flow control 35 and valves 45, 47 and 49 of this example can, if desired, be actuated on a real-time basis to modify the flow rates in the channels 32 and 34 during production and sampling.

The flow rate may be altered to affect the flow of fluid and optimize the intake of virgin fluid into the downhole tool. Various devices may be used to measure and adjust the rates to optimize the fluid flow into the tool. Initially, it may be desirable to have increased flow into the exterior channel when the amount of contaminated fluid is high, and then adjust the flow rate to increase the flow into the interior channel once the amount of virgin fluid entering the probe increases. In this manner, the fluid sampling may be manipulated to increase the efficiency of the sampling process and the quality of the sample.

Referring now to FIGS. 8A and 8B, another embodiment of the present invention employing a fluid sampling system 26b is depicted. A downhole tool 10b is deployed into wellbore 14 on coiled tubing 58. Dual packers 60 extend from the downhole tool 10b and sealingly engage the sidewall 17 of the wellbore 14. The wellbore 14 is lined with mud cake 15 and surrounded by an invaded zone 19. A pair of cylindrical walls or rings 36b are preferably positioned between the packers 60 for isolation from the remainder of the wellbore 14. The packers 60 may be any device capable of sealing the probe from exposure to the wellbore, such as packers or any other suitable device.

The walls 36b are capable of separating fluid extracted from the formation 16 into at least two flow channels 32b and 34b. The tool 10b includes a body 64 having at least one fluid inlet 68 in fluid communication with fluid in the wellbore between the packers 60. The walls 36b are positioned about the body 64. As indicated by the arrows, the walls 36b are axially movable along the tool. Inlets positioned between the walls 36 preferably capture virgin fluid 22, while inlets outside the walls 36 preferably draw in contaminated fluid 20.

The walls 36b are desirably adjustable to optimize the sampling process. The shape and orientation of the walls 36b may be selectively varied to alter the sampling region. The distance between the walls 36b and the borehole wall 17, may be varied, such as by selectively extending and retracting the walls 36b from the body 64. The position of the walls 36b may be along the body 64. The position of the walls along the body 64 may to moved apart to increase the number of intakes 68 receiving virgin fluid, or moved together to reduce the number of intakes receiving virgin fluid depending on the flow characteristics of the formation. The walls 36b may also be centered about a given position along the tool 10b and/or a portion of the borehole 14 to align certain intakes 68 with the flow of virgin fluid 22 into the wellbore 14 between the packers 60.

The position of the movement of the walls along the body may or may not cause the walls to pass over intakes. In some embodiments, the intakes may be positioned in specific regions about the body. In this case, movement of the walls along the body may redirect flow within a given area between the packers without having to pass over intakes. The size of the sampling region between the walls 36b may be selectively adjusted between any number of desirable positions, or within any desirable range, with the use of any suitable component(s) and technique(s).

An example of a flow system for selectively drawing fluid into the downhole tool is depicted in FIG. 8C. A fluid flow line 70 extends from each intake 68 into the downhole tool 10b and has a corresponding valve 72 for selectively diverting fluid to either a sample chamber 75 or into the wellbore outside of the packers 60. One or more pumps 35 may be used in coordination with the valves 72 to selectively draw fluid in at various rates to control the flow of fluid into the downhole tool. Contaminated fluid is preferably dispersed back to the wellbore. However, where it is determined that virgin fluid is entering a given intake, a valve 72 corresponding to the intake may be activated to deliver the virgin fluid to a sample chamber 75. Various measurement devices, such as an OFA 59 may be used to evaluate the fluid drawn into the tool. Where multiple intakes are used, specific intakes may be activated to increase the flow nearest the central flow of virgin fluid, while intakes closer to the contaminated region may be decreased to effectively steer the highest concentration of virgin fluid into the downhole tool for sampling.

One or more probes 28 as depicted in any of FIGS. 3-6J may also be used in combination with the probe 28b of FIG. 8A or 8B.

Figure 9:
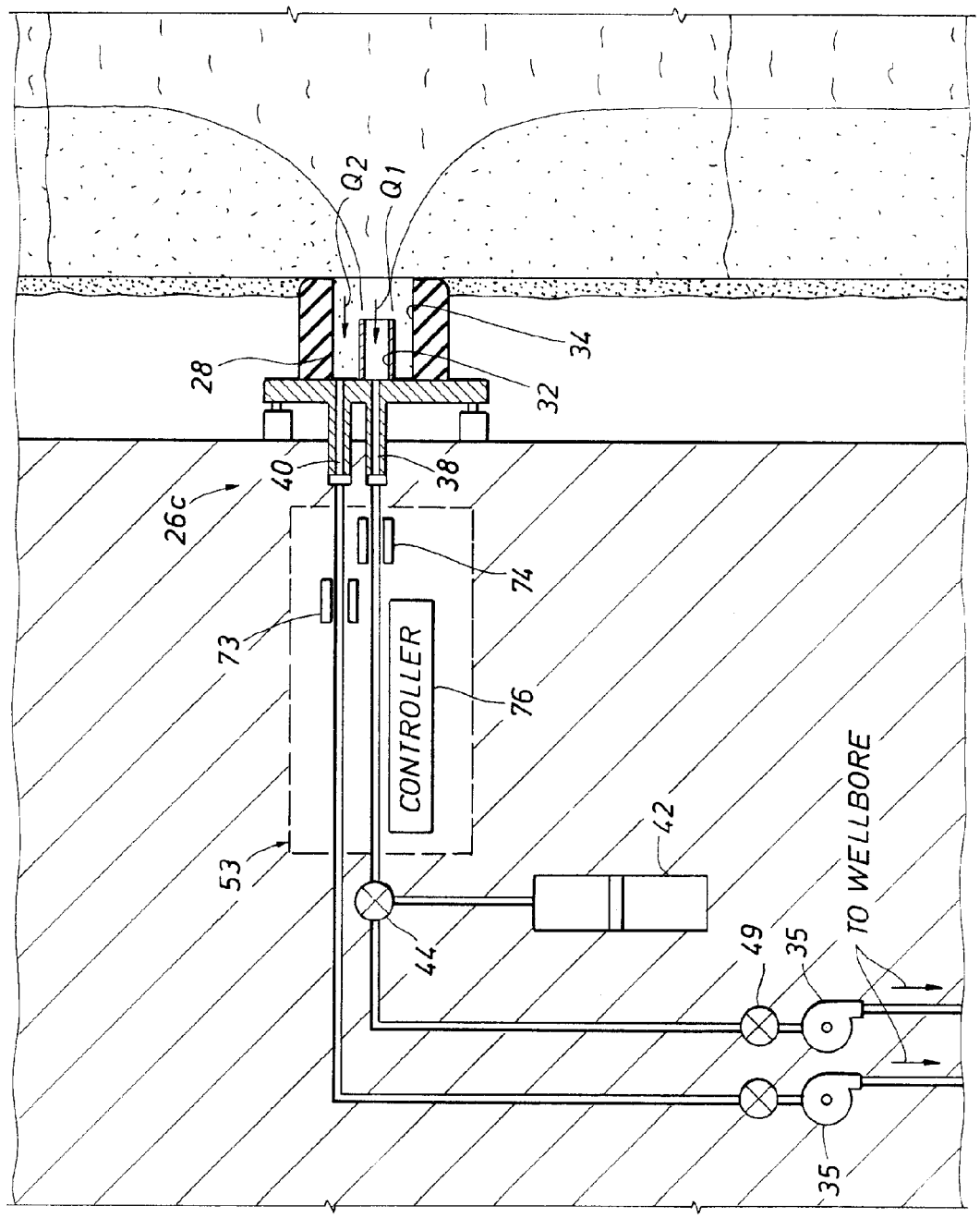
FIG. 9 is a schematic view of the fluid sampling device of FIG. 5 having flow lines with individual pumps.

Referring to FIG. 9, another view of the fluid sampling system 26 of FIG. 5 is shown. In FIG. 9, the flow lines 38 and 40 each have a pump 35 for selectively drawing fluid into the channels 32 and 34 of the probe 28.

The fluid monitoring system 53 of FIG. 5 is shown in greater detail in FIG. 9. The flow lines 38 and 40 each pass through the fluid monitoring system 53 for analysis therein. The fluid monitoring system 53 is provided with an optical fluid analyzer 73 for measuring optical density in flow line 40 and an optical fluid analyzer 74 for measuring optical density in flow line 38. The optical fluid analyzer may be a device such as the analyzer described in U.S. Pat. Nos. 6,178,815 and/or 4,994,671, both of which are hereby incorporated by reference.

While the fluid monitoring system 53 of FIG. 9 is depicted as having an optical fluid analyzer for monitoring the fluid, it will be appreciated that other fluid monitoring devices, such as gauges, meters, sensors and/or other measurement or equipment incorporating for evaluation, may be used for determining various properties of the fluid, such as temperature, pressure, composition, contamination and/or other parameters known by those of skill in the art.

A controller 76 is preferably provided to take information from the optical fluid analyzer(s) and send signals in response thereto to alter the flow of fluid into the interior channel 32 and/or exterior channel 34 of the probe 28. As depicted in FIG. 9, the controller is part of the fluid monitoring system 53; however, it will be appreciated by one of skill in the art that the controller may be located in other parts of the downhole tool and/or surface system for operating various components within the wellbore system.

The controller is capable of performing various operations throughout the wellbore system. For example, the controller is capable of activating various devices within the downhole tool, such as selectively activating the sizer, pivoter, shaper and/or other probe device for altering the flow of fluid into the interior and/or exterior channels 32, 34 of the probe. The controller may be used for selectively activating the pumps 35 and/or valves 44, 45, 47, 49 for controlling the flow rate into the channels 32, 34, selectively activating the pumps 35 and/or valves 44, 45, 47, 49 to draw fluid into the sample chamber(s) and/or discharge fluid into the wellbore, to collect and/or transmit data for analysis uphole and other functions to assist operation of the sampling process. The controller may also be used for controlling fluid extracted from the formation, providing accurate contamination parameter values useful in a contamination monitoring model, adding certainty in determining when extracted fluid is virgin fluid sufficient for sampling, enabling the collection of improved quality fluid for sampling, reducing the time required to achieve any of the above, or any combination thereof. However, the contamination monitoring calibration capability can be used for any other suitable purpose(s). Moreover, the use(s) of, or reasons for using, a contamination monitoring calibration capability are not limiting upon the present invention.

An example of optical density (OD) signatures generated by the optical fluid analyzers 72 and 74 of FIG. 9 is shown in FIG. 10. FIG. 10 shows the relationship between OD and the total volume V of fluid as it passes into the interior and exterior channels of the probe. The OD of the fluid flowing through the interior channel 32 is depicted by line 80. The OD of the fluid flowing through the exterior channel 34 is depicted as line 82. The resulting signatures represented by lines 80 and 82 may be used to calibrate future measurements.

Initially, the OD of fluid flowing into the channels is at $OD_{mf}$. $OD_{mf}$ represents the OD of the contaminated fluid adjacent the wellbore as depicted in FIG. 1. Once the volume of fluid entering the interior channel reaches $V_1$, virgin fluid breaks through. The OD of the fluid entering into the channels increases as the amount of virgin fluid entering into the channels increases. As virgin fluid enters the interior channel 32, the OD of the fluid entering into the interior channel increases until it reaches a second plateau at $V_2$ represented by $OD_{vf}$.

While virgin fluid also enters the exterior channel 34, most of the contaminated fluid also continues to enter the exterior channel. The OD of fluid in the exterior channel as represented by line 82, therefore, increases, but typically does not reach the $OD_{vf}$ due to the presence of contaminants. The breakthrough of virgin fluid and flow of fluid into the interior and exterior channels is previously described in relation to FIG. 2.

The distinctive signature of the OD in the internal channel may be used to calibrate the monitoring system or its device. For example, the parameter $OD_{vf}$, which characterizes the optical density of virgin fluid, can be determined. This parameter can be used as a reference for contamination monitoring. The data generated from the fluid monitoring system may then be used for analytical purposes and as a basis for decision making during the sampling process.

By monitoring the coloration generated at various optical channels of the fluid monitoring system 53 relative to the curve 80, one can determine which optical channel(s) provide the optimum contrast readout for the optical densities $OD_{mf}$ and $OD_{vf}$. These optical channels may then be selected for contamination monitoring purposes.

FIGS. 11A and 11B depict the relationship between the OD and flow rate of fluid into the probe. FIG. 11A shows the OD signatures of FIG. 10 that has been adjusted during sampling. As in FIG. 10, line 80 shows the signature of the OD of the fluid entering the interior channel 32, and 82 shows the signature of the OD of the fluid entering the exterior channel 34. However, FIG. 11A further depicts evolution of the OD at volumes $V_3$, $V_4$ and $V_5$ during the sampling process.

FIG. 11B shows the relationship between the ratio of flow rates $Q_1/Q_2$ to the volume of fluid that enters the probe. As depicted in FIG. 7A, $Q_1$ relates to the flow rate into the interior channel 32, and $Q_2$ relates to the flow rate into the exterior channel 34 of the probe 28. Initially, as mathematically depicted by line 84 of FIG. 11B, the ratio of flow $Q_1/Q_2$ is at a given level $(Q_1/Q_2)_i$ corresponding to the flow ratio of FIG. 7A. However, the ratio $Q_1/Q_2$ can then be gradually increased, as described with respect to FIG. 7B, so that the ratio of $Q_1/Q_2$ increases. This gradual increase in flow ratio is mathematically depicted as the line 84 increases to the level $(Q_1/Q_2)_n$ at a given volume, such as $V_4$. As depicted in FIG. 11B, the ratio can be further increased up to $V_5$.

As the ratio of flow rate increases, the corresponding OD of the interior channel 32 represented by lines 80 shifts to deviation 81, and the OD of the exterior channel 34 represented by line 82 shifts to deviations 83 and 85. The shifts in the ratio of flow depicted in FIG. 11B correspond to shifts in the OD depicted in FIG. 11A for volumes $V_1$ through $V_5$. An increase in the flow rate ratio at $V_3$ (FIG. 11B) shifts the OD of the fluid flowing into the exterior channel from its expected path 82 to a deviation 83 (FIG. 11B). A further increase in ratio, as depicted by line 84 at $V_4$ (FIG. 11A), causes a shift in the OD of line 80 from its reference level $OD_{vf}$ to a deviation 81 (FIG. 11B). The deviation of the OD of line 81 at $V_4$ causes the OD of line 80 to return to its reference level $OD_{vf}$ at $V_5$, while the OD of deviation 83 drops further along deviation 85. Further adjustments to OD and/or ratio may be made to alter the flow characteristics of the sampling process.

Figure 12:
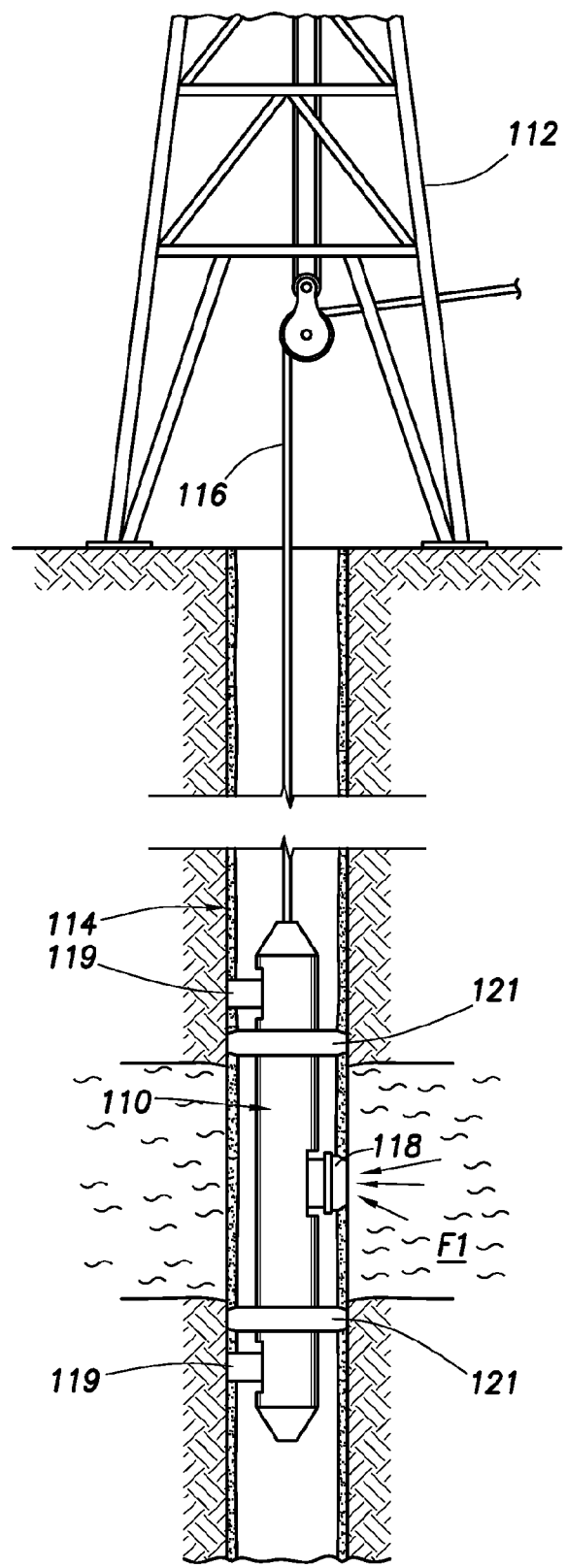
FIG. 12 is a schematic view, partially in cross-section of downhole formation evaluation tool positioned in a wellbore adjacent a subterranean formation.

FIG. 12 depicts another a conventional wireline tool 110 with a probe 118 and fluid flow system. In FIG. 12, the tool 110 is deployed from a rig 112 into a wellbore 114 via a wireline cable 116 and positioned adjacent a formation F1. The downhole tool 110 with probe 118 is adapted to seal with the wellbore wall and draw fluid from the formation into the downhole tool. Dual packers 121 are also depicted to demonstrate that various fluid communication devices, such as probes and/or packers, may be used to draw fluid into the downhole tool. Backup pistons 119 assist in pushing the downhole tool and probe against the wellbore wall.

Figure 13:
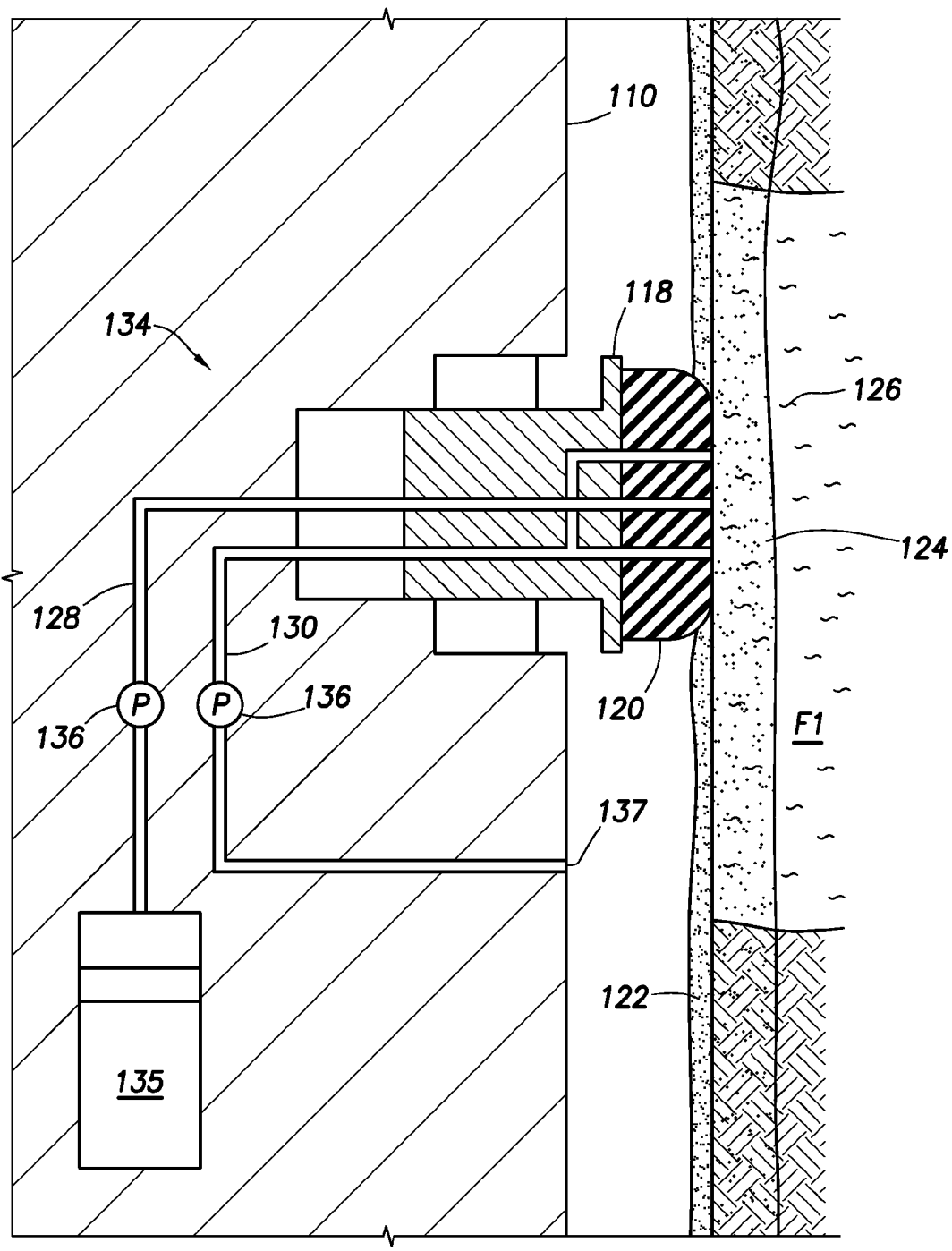
FIG. 13 is a schematic view of a portion of the downhole formation evaluation tool of FIG. 12 depicting a fluid flow system for receiving fluid from the adjacent formation.

FIG. 13 is a schematic view of a portion of the downhole tool 110 of FIG. 12 depicting a fluid flow system 134. The probe 118 is preferably extended from the downhole tool for engagement with the wellbore wall. The probe is provided with a packer 120 for sealing with the wellbore wall. The packer contacts the wellbore wall and forms a seal with the mudcake 122 lining the wellbore. The mudcake seeps into the wellbore wall and creates an invaded zone 124 about the wellbore. The invaded zone contains mud and other wellbore fluids that contaminate the surrounding formations, including the formation F1 and a portion of the clean formation fluid 126 contained therein.

Figure 2:
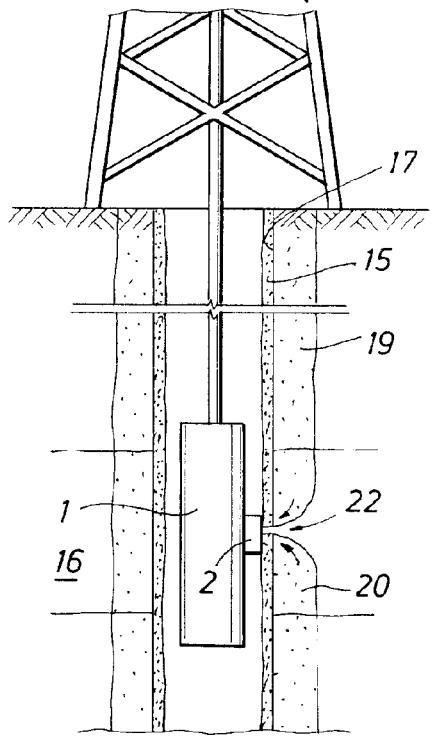
FIG. 2 is a schematic view of a down hole tool positioned in the wellbore with a probe extending to the formation, depicting the flow of contaminated and virgin fluid into a downhole sampling tool.

The probe 118 is preferably provided with at least two flowlines, an evaluation flowline 128 and a cleanup flowline 130. It will be appreciated that in cases where dual packers are used, inlets may be provided therebetween to draw fluid into the evaluation and cleanup flowlines in the downhole tool. Examples of fluid communication devices, such as probes and dual packers, used for drawing fluid into separate flowlines are depicted in FIGS. 1, 2 and 9 above and in U.S. Pat. Nos. 6,719,049 and 6,301,959.

The evaluation flowline extends into the downhole tool and is used to pass clean formation fluid into the downhole tool for testing and/or sampling. The evaluation flowline extends to a sample chamber 135 for collecting samples of formation fluid. The cleanup flowline 130 extends into the downhole tool and is used to draw contaminated fluid away from the clean fluid flowing into the evaluation flowline. Contaminated fluid may be dumped into the wellbore through an exit port 137. One or more pumps 136 may be used to draw fluid through the flowlines. A divider or barrier is preferably positioned between the evaluation and cleanup flowlines to separate the fluid flowing therein.

Figure 14:
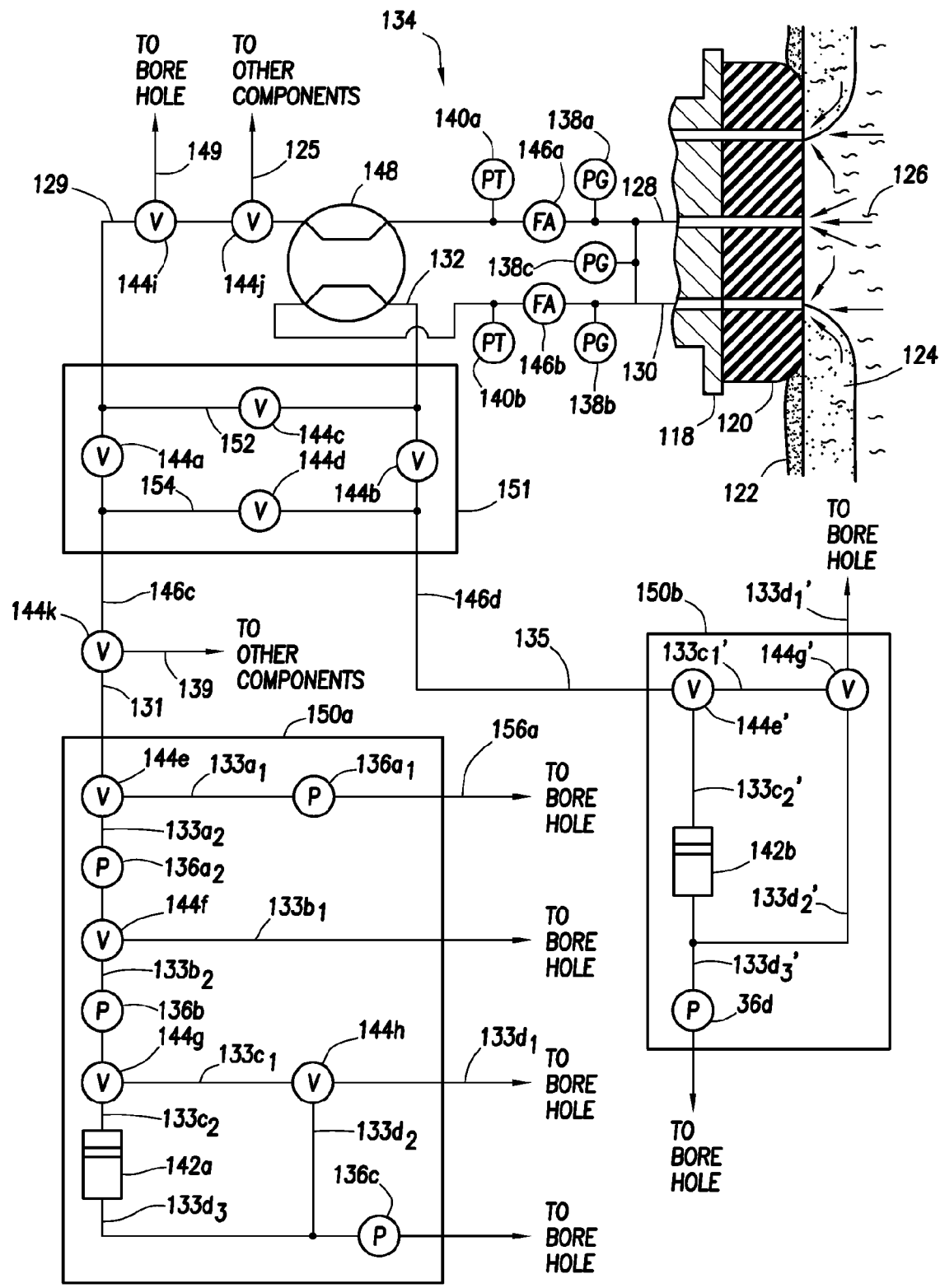
FIG. 14 is a schematic, detailed view of the downhole tool and fluid flow system of FIG. 13.

Referring now to FIG. 14, the fluid flow system 134 of FIG. 13 is shown in greater detail. In this figure, fluid is drawn into the evaluation and cleanup flowlines through probe 118. As fluid flows into the tool, the contaminated fluid in the invaded zone 124 (FIG. 13) breaks through so that the clean fluid 126 may enter the evaluation flowline 128 (FIG. 14). Contaminated fluid is drawn into the cleanup line and away from the evaluation flowline as shown by the arrows. FIG. 14 depicts the probe as having a cleanup flowline that forms a ring about the surface of the probe. However, it will be appreciated that other layouts of one or more intake and flowlines extending through the probe may be used.

The evaluation and cleanup flowlines 128, 130 extend from the probe 118 and through the fluid flow system 134 of the downhole tool. The evaluation and cleanup flowlines are in selective fluid communication with flowlines extending through the fluid flow system as described further herein. The fluid flow system of FIG. 14 includes a variety of features for manipulating the flow of clean and/or contaminated fluid as it passes from an upstream location near the formation to a downstream location through the downhole tool. The system is provided with a variety of fluid measuring and/or manipulation devices, such as flowlines (128, 129, 130, 131, 132, 133, 135), pumps 136, pretest pistons 140, sample chambers 142, valves 144, fluid connectors (148, 151) and sensors (138, 146). The system may also provided with a variety of additional devices, such as restrictors, diverters, processors and other devices for manipulating flow and/or performing various formation evaluation operations.

Evaluation flowline 128 extends from probe 118 and fluidly connects to flowlines extending through the downhole tool. Evaluation flowline 128 is preferably provided with a pretest piston 140a and sensors, such as pressure gauge 138a and a fluid analyzer 146a. Cleanup flowline 130 extends from probe 118 and fluidly connects to flowlines extending through the downhole tool. Cleanup flowline 130 is preferably provided with a pretest piston 140b and sensors, such as a pressure gauge 138b and a fluid analyzer 146b. Sensors, such as pressure gauge 138c, may be connected to evaluation and cleanup flowlines 128 and 130 to measure parameters therebetween, such as differential pressure. Such sensors may be located in other positions along any of the flowlines of the fluid flow system as desired.

One or more pretest piston may be provided to draw fluid into the tool and perform a pretest operation. Pretests are typically performed to generate a pressure trace of the drawdown and buildup pressure in the flowline as fluid is drawn into the downhole tool through the probe. When used in combination with a probe having an evaluation and cleanup flowline, the pretest piston may be positioned along each flowline to generate curves of the formation. These curves may be compared and analyzed. Additionally, the pretest pistons may be used to draw fluid into the tool to break up the mudcake along the wellbore wall. The pistons may be cycled synchronously or at disparate rates to align and/or create pressure differentials across the respective flowlines.

The pretest pistons may also be used to diagnose and/or detect problems during operation. Where the pistons are cycled at different rates, the integrity of isolation between the lines may be determined. Where the change in pressure across one flowline is reflected in a second flowline, there may be an indication that insufficient isolation exists between the flowlines. A lack of isolation between the flowlines may indicate that an insufficient seal exists between the flowlines. The pressure readings across the flowlines during the cycling of the pistons may be used to assist in diagnosis of any problems, or verification of sufficient operability.

The fluid flow system may be provided with fluid connectors, such as crossover 148 and/or junction 151, for passing fluid between the evaluation and cleanup flowlines (and/or other flowlines fluidly connected thereto). These devices may be positioned at various locations along the fluid flow system to divert the flow of fluid from one or more flowlines to desired components or portions of the downhole tool. As shown in FIG. 14, a rotatable crossover 148 may be used to fluidly connect evaluation flowline 128 with flowline 132, and cleanup flowline 130 with flowline 129. In other words, fluid from the flowlines may selectively be diverted between various flowlines as desired. By way of example, fluid may be diverted from flowline 128 to flow circuit 150b, and fluid may be diverted from flowline 130 to flow circuit 150a.

Junction 151 is depicted in FIG. 14 as containing a series of valves 144a, b, c, d and associated connector flowlines 152 and 154. Valve 144a permits fluid to pass from flowline 129 to connector flowline 154 and/or through flowline 131 to flow circuit 150a. Valve 144b permits fluid to pass from flowline 132 to connector flowline 154 and/or through flowline 135 to flow circuit 150b. Valve 144c permits fluid to flow between flowlines 129, 132 upstream of valves 144a and 144b. Valve 144d permits fluid to flow between flowlines 131, 135 downstream of valves 144a and 144b. This configuration permits the selective mixing of fluid between the evaluation and cleanup flowlines. This may be used, for example, to selectively pass fluid from the flowlines to one or both of the sampling circuits 150a, b.

Valves 144a and 144b may also be used as isolation valves to isolate fluid in flowline 129, 132 from the remainder of the fluid flow system located downstream of valves 144a, b. The isolation valves are closed to isolate a fixed volume of fluid within the downhole tool (i.e., in the flowlines between the formation and the valves 144a, b). The fixed volume located upstream of valve 144a and/or 144b is used for performing downhole measurements, such as pressure and mobility.

In some cases, it is desirable to maintain separation between the evaluation and cleanup flowlines, for example during sampling. This may be accomplished, for example, by closing valves 144c and/or 144d to prevent fluid from passing between flowlines 129 and 132, or 131 and 135. In other cases, fluid communication between the flowlines may be desirable for performing downhole measurements, such as formation pressure and/or mobility estimations. This may be accomplished for example by closing valves 144a, b, opening valves 144c and/or 144d to allow fluid to flow across flowlines 129 and 132 or 131 and 135, respectively. As fluid flows into the flowlines, the pressure gauges positioned along the flowlines can be used to measure pressure and determine the change in volume and flow area at the interface between the probe and formation wall. This information may be used to generate the formation mobility.

Valves 144c, d may also be used to permit fluid to pass between the flowlines inside the downhole tool to prevent a pressure differential between the flowlines. Absent such a valve, pressure differentials between the flowlines may cause fluid to flow from one flowline, through the formation and back into another flowline in the downhole tool, which may alter measurements, such as mobility and pressure.

Junction 151 may also be used to isolate portions of the fluid flow system downstream thereof from a portion of the fluid flow system upstream thereof. For example, junction 151 (i.e., by closing valves 144a, b) may be used to pass fluid from a position upstream of the junction to other portions of the downhole tool, for example through valve 144j and flowline 125 thereby avoiding the fluid flow circuits. In another example, by closing valves 144a, b and opening valve d, this configuration may be used to permit fluid to pass between the fluid circuits 150 and/or to other parts of the downhole tool through valve 144k and flowline 139. This configuration may also be used to permit fluid to pass between other components and the fluid flow circuits without being in fluid communication with the probe. This may be useful in cases, for example, where there are additional components, such as additional probes and/or fluid circuit modules, downstream of the junction.

Junction 151 may also be operated such that valve 144a and 144d are closed and 144b and 144c are open. In this configuration, fluid from both flowlines may be passed from a position upstream of junction 151 to flowline 135. Alternatively, valves 144b and 144d may be closed and 144a and 144c are open so that fluid from both flowlines may be passed from a position upstream of junction 151 to flowline 131.

The flow circuits 150a and 150b (sometimes referred to as sampling or fluid circuits) preferably contain pumps 136, sample chambers 142, valves 144 and associated flowlines for selectively drawing fluid through the downhole tool. One or more flow circuits may be used. For descriptive purposes, two different flow circuits are depicted, but identical or other variations of flow circuits may be employed.

Flowline 131 extends from junction 151 to flow circuit 150a. Valve 144e is provided to selectively permit fluid to flow into the flow circuit 150a. Fluid may be diverted from flowline 131, past valve 144e to flowline 133a1 and to the borehole through exit port 156a. Alternatively, fluid may be diverted from flowline 131, past valve 144e through flowline 133a2 to valve 144f. Pumps 136a1 and 136a2 may be provided in flowlines 133a1 and 133a2, respectively.

Fluid passing through flowline 133a2 may be diverted via valve 144f to the borehole via flowline 133b1, or to valve 144g via flowline 133b2. A pump 136b may be positioned in flowline 133b2.

Fluid passing through flowline 133b2 may be passed via valve 144g to flowline 133c1 or flowline 133c2. When diverted to flowline 133c1, fluid may be passed via valve 144h to the borehole through flowline 133d1, or back through flowline 133d2. When diverted through flowline 133c2, fluid is collected in sample chamber 142a. Buffer flowline 133d3 extends to the borehole and/or fluidly connects to flowline 133d2. Pump 136c is positioned in flowline 133d3 to draw fluid therethrough.

Flow circuit 150b is depicted as having a valve 144e' for selectively permitting fluid to flow from flowline 135 into flow circuit 150b. Fluid may flow through valve 144e' into flowline 133c1', or into flowline 133c2' to sample chamber 142b. Fluid passing through flowline 133c1' may be passed via valve 144g' to flowline 133d1' and out to the borehole, or to flowline 133d2'. Buffer flowline 133d3' extends from sample chamber 142b to the borehole and/or fluidly connects to flowline 133d2'. Pump 136d is positioned in flowline 13343' to draw fluid therethrough.

A variety of flow configurations may be used for the flow control circuit. For example, additional sample chambers may be included. One or more pumps may be positioned in one or more flowlines throughout the circuit. A variety of valving and related flowlines may be provided to permit pumping and diverting of fluid into sample chambers and/or the wellbore.

The flow circuits may be positioned adjacently as depicted in FIG. 14. Alternatively, all or portions of the flow circuits may be positioned about the downhole tool and fluidly connected via flowlines. In some cases, portions of the flow circuits (as well as other portions of the tool, such as the probe) may be positioned in modules that are connectable in various configurations to form the downhole tool. Multiple flow circuits may be included in a variety of locations and/or configurations. One or more flowlines may be used to connect to the one or more flow circuits throughout the downhole tool.

An equalization valve 144i and associated flowline 149 are depicted as being connected to flowline 129. One or more such equalization valves may be positioned along the evaluation and/or cleanup flowlines to equalize the pressure between the flowline and the borehole. This equalization allows the pressure differential between the interior of the tool and the borehole to be equalized, so that the tool will not stick against the formation. Additionally, an equalization flowline assists in assuring that the interior of the flowlines is drained of pressurized fluids and gases when it rises to the surface. This valve may exist in various positions along one or more flowlines. Multiple equalization valves may be employed, particularly where pressure is anticipated to be trapped in multiple locations. Alternatively, other valves 144 in the tool may be configured to automatically open to allow multiple locations to equalize pressure.

A variety of valves may be used to direct and/or control the flow of fluid through the flowlines. Such valves may include check valves, crossover valves, flow restrictors, equalization, isolation or bypass valves and/or other devices capable of controlling fluid flow. Valves 144a-k may be on-off valves that selectively permit the flow of fluid through the flowline. However, they may also be valves capable of permitting a limited amount of flow therethrough. Crossover 148 is an example of a valve that may be used to transfer flow from the evaluation flowline 128 to the first sampling circuit and to transfer flow from the cleanup flowline to the second sampling circuit, and then switch the sampling flowing to the second sampling circuit and the cleanup flowline to the first sampling circuit.

One or more pumps may be positioned across the flowlines to manipulate the flow of fluid therethrough. The position of the pump may be used to assist in drawing fluid through certain portions of the downhole tool. The pumps may also be used to selectively flow fluid through one or more of the flowlines at a desired rate and/or pressure. Manipulation of the pumps may be used to assist in determining downhole fluid properties, such as formation fluid pressure, formation fluid mobility, etc. The pumps are typically positioned such that the flowline and valving may be used to manipulate the flow of fluid through the system. For example, one or more pumps may be upstream and/or downstream of certain valves, sample chambers, sensors, gauges or other devices.

The pumps may be selectively activated and/or coordinated to draw fluid into each flowline as desired. For example, the pumping rate of a pump connected to the cleanup flowline may be increased and/or the pumping rate of a pump connected to the evaluation flowline may be decreased, such that the amount of clean fluid drawn into the evaluation flowline is optimized. One or more such pumps may also be positioned along a flowline to selectively increase the pumping rate of the fluid flowing through the flowline.

One or more sensors (sometimes referred to herein as fluid monitoring devices), such as the fluid analyzers 146a, b (i.e., the fluid analyzers described in U.S. Pat. No. 4,994,671) and pressure gauges 138a, b, c, may be provided. A variety of sensors may be used to determine downhole parameters, such as content, contamination levels, chemical (e.g., percentage of a certain chemical/substance), hydro mechanical (viscosity, density, percentage of certain phases, etc.), electromagnetic (e.g., electrical resistivity), thermal (e.g., temperature), dynamic (e.g., volume or mass flow meter), optical (absorption or emission), radiological, pressure, temperature, salinity, Ph, radioactivity (gamma, neutron and spectral energy), carbon content, clay composition and content, oxygen content, and/or other data about the fluid and/or associated downhole conditions, among others. As described above, fluid analyzers may collect optical measurements, such as optical density. Sensor data may be collected, transmitted to the surface and/or processed downhole.

Preferably, one or more of the sensors are pressure gauges 138 positioned in the evaluation flowline (138a), the cleanup flowline (138b) or across both for differential pressure therebetween (138c). Additional gauges maybe positioned at various locations along the flowlines. The pressure gauges maybe used to compare pressure levels in the respective flowlines, for fault detection, or for other analytical and/or diagnostic purposes. Measurement data may be collected, transmitted to the surface and/or processed downhole. This data, alone or in combination with the sensor data may be used to determine downhole conditions and/or make decisions.

One or more sample chambers may be positioned at various positions along the flowline. A single sample chamber with a piston therein is schematically depicted for simplicity. However, it will be appreciated that a variety of one or more sample chambers may be used. The sample chambers may be interconnected with flowlines that extend to other sample chambers, other portions of the downhole tool, the borehole and/or other charging chambers. Examples of sample chambers and related configures may be seen in U.S. Patent Application Publication No. 2003/0042021 and U.S. Pat. Nos. 6,467,544 and 6,659,177. Preferably, the sample chambers are positioned to collect clean fluid. Moreover, it is desirable to position the sample chambers for efficient and high quality receipt of clean formation fluid. Fluid from one or more of the flowlines may be collected in one or more sample chambers and/or dumped into the borehole. There is no requirement that a sample chamber be included, particularly for the cleanup flowline that may contain contaminated fluid.

In some cases, the sample chambers and/or certain sensors, such as a fluid analyzer, may be positioned near the probe and/or upstream of the pump. It is often beneficial to sense fluid properties from a point closer to the formation, or the source of the fluid. It may also be beneficial to test and/or sample upstream of the pump. The pump typically agitates the fluid passing through the pump. This agitation can spread the contamination to fluid passing through the pump and/or increase the amount of time before a clean sample may be obtained. By testing and sampling upstream of the pump, such agitation and spread of contamination may be avoided.

Computer or other processing equipment is preferably provided to selectively activate various devices in the system. The processing equipment may be used to collect, analyze, assemble, communicate, respond to and/or otherwise process downhole data. The downhole tool may be adapted to perform commands in response to the processor. These commands may be used to perform downhole operations.

In operation, the downhole tool 110 (FIG. 12) is positioned adjacent the wellbore wall and the probe 118 is extended to form a seal with the wellbore wall. Backup pistons 119 are extended to assist in driving the downhole tool and probe into the engaged position. One or more pumps 136 in the downhole tool are selectively activated to draw fluid into one or more flowlines (FIG. 14). Fluid is drawn into the flowlines by the pumps and directed through the desired flowlines by the valves.

Pressure in the flowlines may also be manipulated using other device to increase and/or lower pressure in one or more flowlines. For example, pistons in the sample chambers and pretest may be retracted to draw fluid therein. Charging, valving, hydrostatic pressure and other techniques may also be used to manipulate pressure in the flowlines.

The flowlines of FIG. 14 may be provided with various sensors, such as fluid analyzer 146a in evaluation flowline 128 and fluid analyzer 146b in cleanup flowline 130. Additional sensors, 146c and 146d may also be provided at various locations along evaluation and cleanup flowlines 131 and 135, respectively. These sensors are preferably capable of measuring fluid properties, such as optical density, or other properties as described above. It is also preferable that these sensors be capable of detecting parameters that assist in determining contamination in the respective flowlines.

The sensors are preferably positioned along the flowlines such that the contamination in one or more flowlines may be determined. For example, when the valves are selectively operated such that fluid in flowlines 128 and 130 passes through sensor 146a and 146b, a measurement of the contamination in these separate flowlines may be determined. The fluid in the separate flowlines may be co-mingled or joined into a merged or combined flowline. A measurement may then be made of the fluid properties in such merged or combined flowlines.

The fluid in flowlines 128 and 130 may be merged by diverting the fluid into a single flowline. This may be done, for example, by selectively closing certain valves, such as valves 144a and 144d, in junction 151. This will divert fluid in both flowlines into flowline 135. It is also possible to obtain a merged flowline measurement by permitting flow into probe 120 using flowline 128 or 130, rather than both. A combined or merged flowline may also be fluidly connected to one or more inlets in the probe such that fluid that enters the tool is co-mingled in a single or combined flowline.

It is also possible to selectively switch between merged and separate flowlines. Such switching may be done automatically or manually. It may also be possible to selectively adjust pressures between the flowlines for relative pressure differentials therebetween. Fluid passing through only flowline 128 may be measured by sensor 146a. Fluid passing through only flowline 130 may be measured by sensor 146b.

The flow through flowlines 128 and 130 may be manipulated to selectively permit fluid to pass through one or both flowlines. Fluid may be diverted and/or pumping through one or more flowlines adjusted to selectively alter flow and/or contamination levels therein. In this manner, fluid passing through various sensors may be fluid from evaluation flowline 128, cleanup flowline 130 or combinations thereof. Flow rates may also be manipulated to vary the flow through one or more of the flowlines. Fluid passing through the individual and/or merged flowlines may then be measured by sensors in the respective flowlines. For example, once merged into flowline 135, the fluid may be measured by sensor 146d.

Using the flow manipulation techniques described with respect to FIG. 14, fluid may be manipulated as desired to selectively flow past certain sensors to take measurements and/or calibrate sensors. The sensors may be calibrated by selectively passing fluid across the sensors and comparing measurements. Calibration may occur simultaneously by drawing fluid into two lines simultaneously and comparing the readings. Calibration may also occur sequentially by comparing readings of the same fluid as it passes multiple sensors to verify consistent readings. Calibration may also occur by recirculating the same fluid past one or more sensor in a flowline.

The fluid from separate flowlines may also be compared and analyzed to detect various downhole properties. Such measurements may then be used to determine contamination levels in the respective flowlines. An analysis of these measurements may then be used to evaluate properties based on merged flowline data and the flowline data in individual flowlines.

A simulated merged flowline may be achieved by mathematically combining the fluid properties of the evaluation and cleanup flowlines. By combining the measurements taken at sensors for each of the separate evaluation and cleanup flowlines, a combined or merged flowline measurement may be determined. Thus, a merged flowline parameter may be obtained either mathematically or by actual measurement of fluid combined in a single flowline.

Figure 15A:
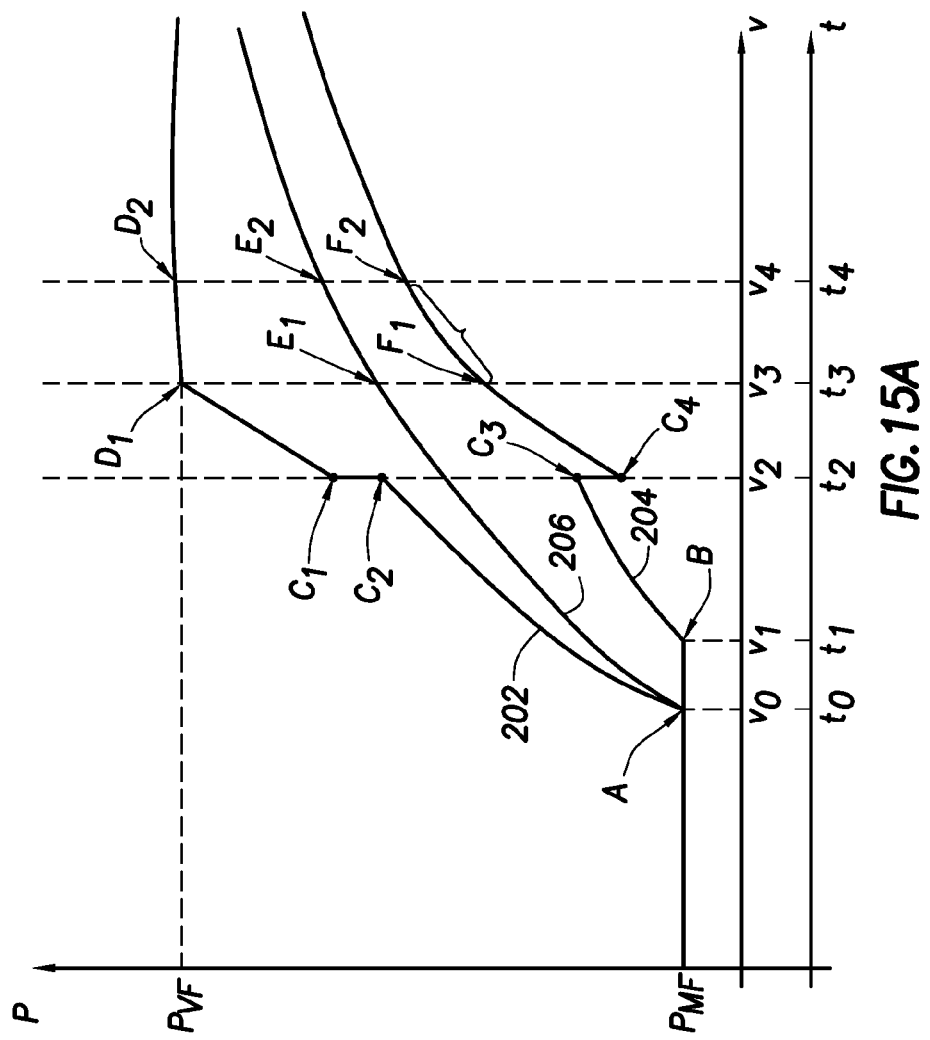
FIG. 15A is a graph of a fluid property of flowlines of the fluid flow system of FIG. 14 using a flow stabilization technique.
Figure 15B:
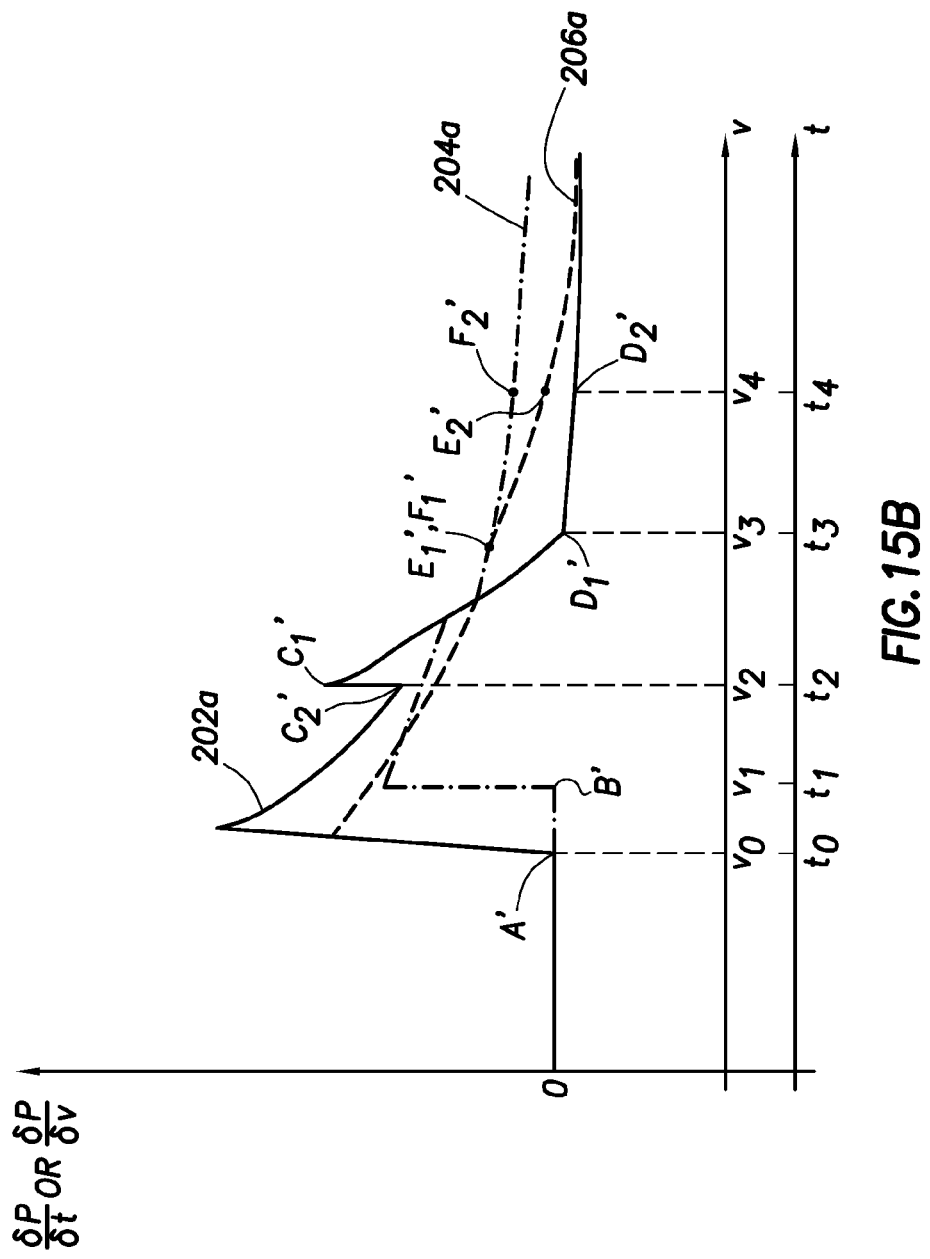
FIG. 15B is a graph of derivatives of the property functions of FIG. 15A.

FIGS. 15A and 15B describe techniques for analyzing contamination of fluid passing into a downhole tool, such as the tool of FIG. 14, using a stabilization technique. FIG. 15A depicts a graph of a fluid property P measured across an evaluation flowline (such as 128 of FIG. 4), a cleanup flowline (such as 130 of FIG. 4) and a merged flowline (such as 135 of FIG. 4) using a stabilization technique. The merged flowline may be generated by co-mingling fluid in the evaluation and cleanup flowlines, or by mathematically determining fluid properties for a merged flowline as described above.

The graph depicts the relationship between a fluid property P (y-axis) versus fluid volume (x-axis) or time (x-axis) for the flowlines. The fluid property may be, for example, the optical density of fluid passing through the flowlines. Other fluid properties may be measured, analyzed, predicted and/or determined using methods provided herein. Preferably, the volume is the total volume withdrawn into the tool through one or more flowlines.

The fluid property P is a physical property of the fluid that distinguishes between mud filtrate and virgin fluid. The property depicted in FIG. 15A is, for example, an optical property, such as optical density, measurable using a fluid analyzer. Mixing laws establish that the physical property P is a function of and corresponds to a contamination level according to the following equation:

$$P = cPmf + (1-c)Pvf \quad (1)$$

where Pmf is the mud filtrate property corresponding to a contamination level of 1 or 100% contamination, Pvf is a virgin fluid property corresponding to a contamination level of 0 or 0% and c is the level of contamination for the fluid. Rearranging the equation generates the following contamination level c for a given fluid property:

$$c = (P - Pvf)/(Pmf - Pvf) \quad (2)$$

The fluid property may be graphically expressed in relationship to time or volume as shown in FIG. 15A. In other words, the x-axis may be represented in terms of volume or time given the known relationship of time and volume through flowrate.

In the example shown in FIG. 15A, fluid is drawn into evaluation flowline 128, cleanup flowline 130, and passes through sensors 146a and 146b. A merged flowline measurement may be obtained by combining the measurements taken by sensors 146a and 146b, or by merging the fluid into a single flowline, for example into flowline 135 for measurement by sensor 146d as described above. The resulting data for the evaluation flowline, cleanup flowline and merged flowline are depicted as lines 202, 204 and 206, respectively.

Fluid is drawn into the flowlines from time 0, volume 0 until time t0, volume v0. Initially, the fluid property P is registered at Pmf (mud filtrate). As described above, Pmf relates to the optical density level that is present when mud filtrate is lining the wellbore wall as shown in FIG. 1. The contamination level at Pmf is assumed to be a high level, such as about 100%. At this point A, the virgin fluid breaks through the mud cake and begins to pass through the flowlines as shown in FIG. 2. The increase in the fluid property measurement reads as an increase in property P along the Y axis. The cleanup flowline typically does not begin to increase until point B at time t1 and volume V1. At point B, a portion of the clean fluid begins to enter the cleanup flowline.

Points C1-C4 show that variations in flow rates may alter the fluid property measurement in the flowline. At time t2 and volume V2, the fluid property measurement in the evaluation flowline shifts from C2 to C1, and the fluid property measurement in the cleanup flowline shifts from C3 to C4 as the flow rates therein are shifted. In this case, the flow in cleanup flowline 130 is increased relative to the flow rate in evaluation flowline 128 thereby decreasing the fluid property measurement in the cleanup flowline while increasing the fluid property measurement in the evaluation flowline. This may, for example, show an increase in clean fluid from points C2 to C1 and a decrease in clean fluid in line 204 from points C3 to C4. While FIG. 15A shows that a shift has occurred as a specific shift in flow rate, flow may decrease in the cleanup line and/or an increase in flow rate in the evaluation flowline, or remain the same in both flowlines.

As flow into the tool continues, the fluid property of the merged flowline is steadily increasing as indicated by line 206. However, the fluid property of the evaluation flowline increases until a stabilization level is reached at point D1. At point D1, the fluid property in the evaluation flowline is at or near Pvf. As described above with respect to FIGS. 11A-C, Pvf at point D1 is considered to be the time when only virgin fluid is passing into the evaluation flowline. At Pvf, the fluid in the evaluation flowline is assumed to be virgin, or at a contamination level of at or approaching zero.

At time t3 and volume V3, the evaluation flowline is essentially drawing in clean fluid, while the cleanup flowline is still drawing in contaminated fluid. The fluid property measurement in flowline 128 remains stabilized through time t4 and volume V4 at point D2. In other words, the fluid property measurement at point D2 is approximately equal to the fluid property measurement at point D1.

From time t3 to t4 and volume V3 to V4, the fluid property in the merged and cleanup flowlines continue to increase as shown at points E1 and E2 of line 206 and points F1 and F2 of line 204, respectively. This indicates that contamination is still flowing into the contaminated and/or merged flowlines, but that the contamination level continues to lower.

As shown in FIG. 15B, the properties depicted in the graph of FIG. 15A may also be depicted based on derivatives of the measurements taken. FIG. 15B depicts the relationship between the derivative of the fluid property versus volume and time, or $\partial P/\partial t$. The evaluation, cleanup and merged flowlines are shown as lines 202a, 204a and 206a, respectively. Points A-F2 correspond to points A'-F2', respectively. Thus, stabilization of the evaluation flowline occurs from points D1' to D2' at $\partial P/\partial t \approx 0$, and fluid property measurements in the merged and cleanup flowlines continue to increase from points E1' to E2' and F1' to F2' where $\partial P/\partial t > 0$. While only a first level derivative is depicted, higher orders of derivatives may be used.

Stabilization of fluid properties in the evaluation flowline from points D1 to D2 can be considered as an indication that complete cleanup is achieved or approached. The stabilization can be verified by determining whether one or more additional events occurred during cleanup monitoring. Such events may include, for example, break through of virgin formation fluid on the evaluation and/or cleanup flowlines (points A and/or B on FIG. 15A) through the probe prior to stabilization (points D1-D2 on FIG. 15A), continued variation of fluid property in the cleanup and/or merged flowline (points E1 to E2 and/or F1 or F2 on FIG. 15A) and/or continued variation in the direction consistent with clean up in the cleanup and/or merged flowline.

As soon as stabilization of the fluid property in the evaluation flowline is confirmed, cleanup may be assumed to have occurred in the evaluation flowline. Such cleanup means that a minimum contamination level has been achieved for the evaluation flowline. Typically, that cleanup results in a virgin fluid passing through the evaluation flowline. This method does not require contamination quantification and is based at least in part on qualitative detection of fluid property variation signature.

The graph of FIG. 15A shows that the amount virgin fluid is entering the flowlines is increasing. As contamination in the flowline is reduced, 'cleanup' occurs. In other words, more and more contaminated fluid is removed so that more virgin fluid enters the tool. In particular, cleanup occurs when virgin fluid enters the evaluation flowline. The increase in virgin fluid is reflected as an increase in fluid properties. However, it will be appreciated that in some cases, cleanup may not occur due to a bad seal or other problems. In such cases where the fluid property fails to increase, this may indicate a problem in the formation evaluation process.

Figure 16:
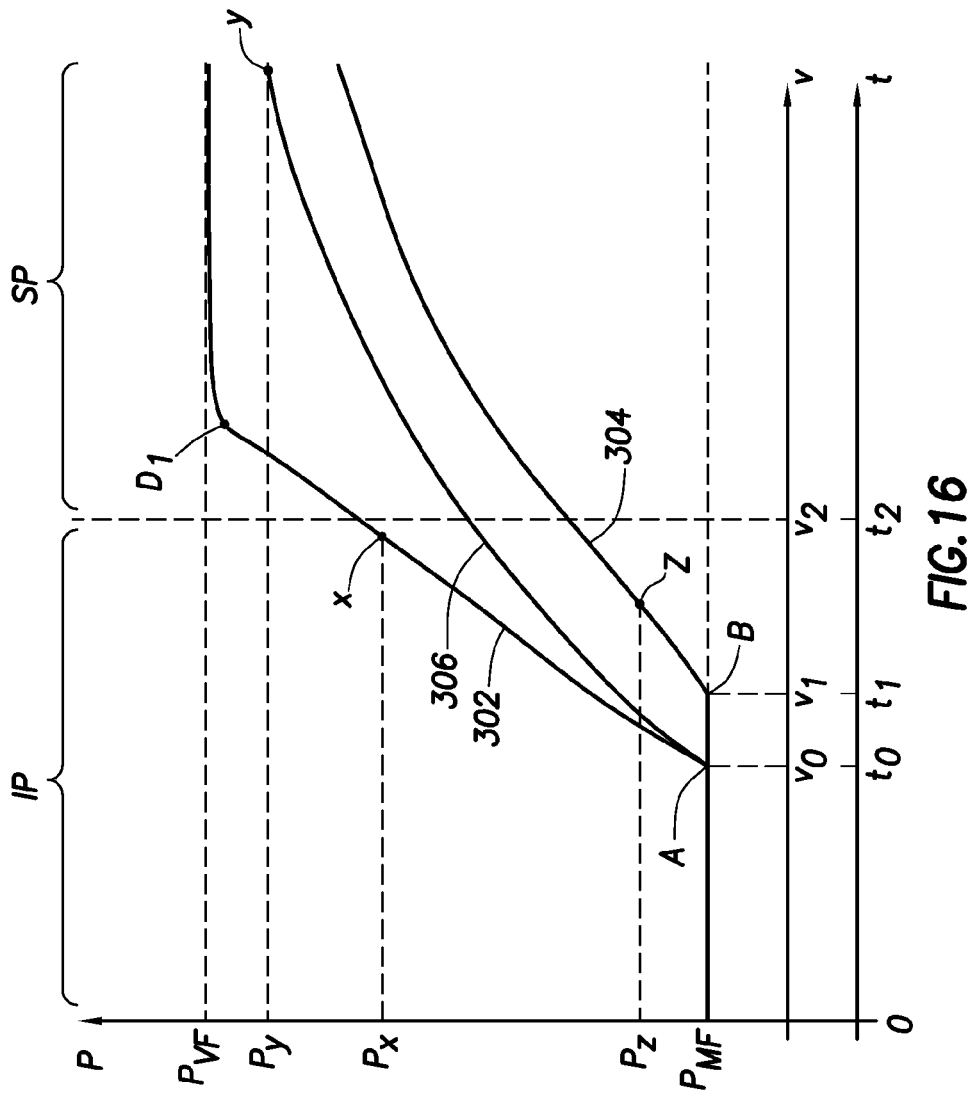
FIG. 16 is a graph of a fluid property of the flowlines of the fluid flow system of FIG. 14 using a projection technique.

FIG. 16 shows a graph of the relationship between a fluid property P versus time and volume using a projection technique. The fluid may be drawn into the tool using the evaluation and/or cleanup flowlines as previously described with respect to FIG. 14. FIG. 16 also depicts that the selective merging of the contamination and cleanup flowlines may be used to generate a merged flowline.

As shown in FIG. 16, fluid is drawn into the downhole tool and a fluid property in the flowline(s) is measured. The technique of FIG. 16 may be accomplished by drawing fluid into a single or merged flowline in the tool during an initial phase IP, and then switching so that fluid is drawn into the tool using an evaluation and a cleanup flowline during a secondary phase SP. In one example, this is done by allowing fluid through the evaluation flowline to generate a merged line 306 as described above with respect to FIG. 14. Alternatively, fluid may be drawn into an evaluation flowline and a cleanup flowline to generate lines 302 and 304, respectively. A resultant merged line 306 may be generated by mathematically determining the combined contamination, or by merging the flowlines and measuring the resultant contamination in the tool as described above.

The merged flowline may extend from the initial phase and continue to generate a curve 306 through the secondary phase. The separate evaluation and cleanup flowlines may also extend from the initial phase and continue to generate their curves 302, 304 through the secondary phase. In some cases, the separate evaluation and cleanup curves may extend through only the initial phase or only the secondary phase. In some cases, the merged evaluation curve may extend through only the initial phase or only the secondary phase. Various combinations of each of the curves may be provided.

In some cases, it may be desirable to start with merged or flow through a single flowline. In particular, it may be desirable to use single or merged flow until virgin fluid break through occurs. This may have the beneficial effect of relieving pressure on the probe and preventing failure of the probe packer(s). The pressure differentials between the flowlines may be manipulated to protect the probe, prevent cross flow, reduce contamination and/or prevent failures.

This merging of the flowlines may be accomplished by manipulating the apparatus of FIG. 14 or mathematically generating the combined flowline as described above. The sensors may be used to measure a fluid property, such as optical density, and a flow rate for each of the evaluation, cleanup and/or combined flowlines.

For illustrative purposes the evaluation, cleanup and merged flowlines will be shown through both the initial and secondary phases. As shown in FIG. 16, fluid is drawn into the tool from a time 0 and volume 0 with a fluid property at Pmf. At time t0 and volume V0 at point A, the virgin fluid breaks through the mudcake and clean fluid begins to enter the tool. At point A, the fluid properties for the merged and evaluation flowlines begin to increase. The merged flowline fluid property increased through the secondary phase through a level Py at point Y as indicated by line 306. The evaluation flowline fluid property continues to increase through point X at a level Py and into the secondary phase, but begins to stabilize at a point D1 at or near the fluid property level Pvf. The cleanup flowline remains at level Pmf until it reaches point B at time t1 and volume V1. The fluid property for the cleanup flowline increases through a fluid property level PZ at point Z through the second phase SP.

The flow rates as depicted in FIG. 16 remain constant, but may also shift as shown at points C1-2 of FIG. 15A. The stabilization level of the evaluation flowline may also be determined in FIG. 16 using the techniques described in FIG. 15A.

Figure 17:
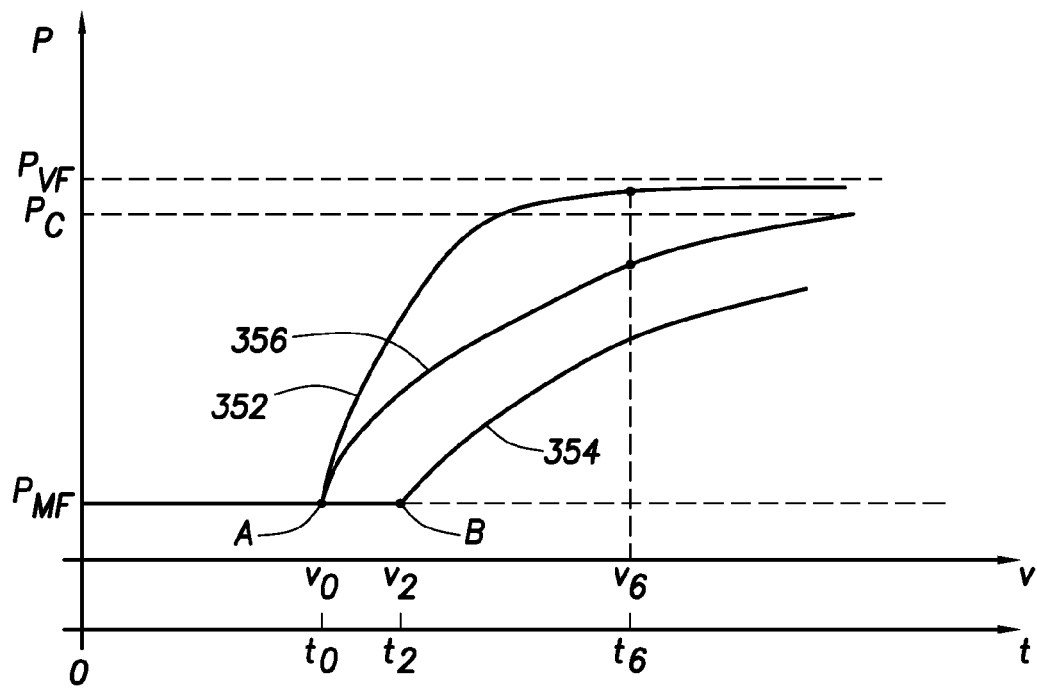
FIG. 17 is a graph depicting the contamination models for merged and a separate flowlines.

FIG. 17 shows a graph of the relationship between the measured fluid property in an evaluation flowline (352) and a merged flowline (356). Both flowlines begin at the level Pmf indicating a high contamination level before breakthrough. At time t0 and volume V0, breakthrough occurs at point A and contamination levels begin to drop as the fluid property increases. Break through for the contamination line occurs at point B at time t2 and volume V2. At time t6, volume V6, the evaluation flowline begins to stabilize, while the combined flowline continues a slower but steady increase. According to known techniques, the combined flowline will continue to draw some portion of contamination fluid and reach a fluid property level Pc below the zero contamination level of Pvf However, the evaluation flowline will begin to approach a zero contamination level at Pvf.

An estimate of Pvf and Pmf may be determined using various techniques. Pmf may be determined by measuring a fluid property prior to virgin fluid break through (point A on FIG. 16). Pmf may also be estimated, for example based on empirical data or known properties, such as the specific mud used in the wellbore.

Pvf may be determined by a variety of methods using a merged or combined flowline. A combined flowline is created using the techniques described above with reference to FIG. 14. In one example using the equation below under a known mixing law, for each time and/or volume a weighted combined fluid property value Pt can be calculated:

$$Pt=(PsQs+PgQg)/(Qs+Qg) \quad (3)$$

where Ps is the fluid property value in the evaluation flowline, Pg is the fluid property in the cleanup flowline, Qs is the flow rate in the evaluation flowline and Qg is the flow rate in the cleanup flowline. The values Pt over the sampling interval may then be plotted to define, for example, a line 356 for the merged flowline. Further information concerning various mixing laws that can be used to generate equation (3) or variations thereof are described in PCT Application Publication No. WO 2005065277.

From the fluid properties represented by line 356, Pvf may be determined, for example, by applying the contamination modeling techniques as described in P. S. Hammond, "One or Two Phased Flow During fluid Sampling by a Wireline Tool," Transport in Porous Media, Vol. 6, p. 299-330 (1991). The Hammond models may then be applied using the relationship between contamination and a fluid property using equation (2). Using this application of the Hammond technique, Pvf may be estimated. Other methods, such as the curve fit techniques described in PCT Application No. 00/50876, based on combined flowline properties, may also be used to determine Pvf.

Once Pmf and Pvf are determined, a contamination level for any flowline may be determined. A fluid property, such as Px, Py or Pz is measured for the desired flowline at points X, Y and Z on the graph of FIG. 16. The contamination level of each of the flowlines may be determined based on the properties of the merged flowline. Once Pvf and Pmf are known, and one parameter, such as Px, Py or Pz, on a given flowline is known, then the contamination level for that flowline can be determined. For example, in order to determine a contamination level at Px, Py or Pz, equation (2) above may be used.

Figure 18:
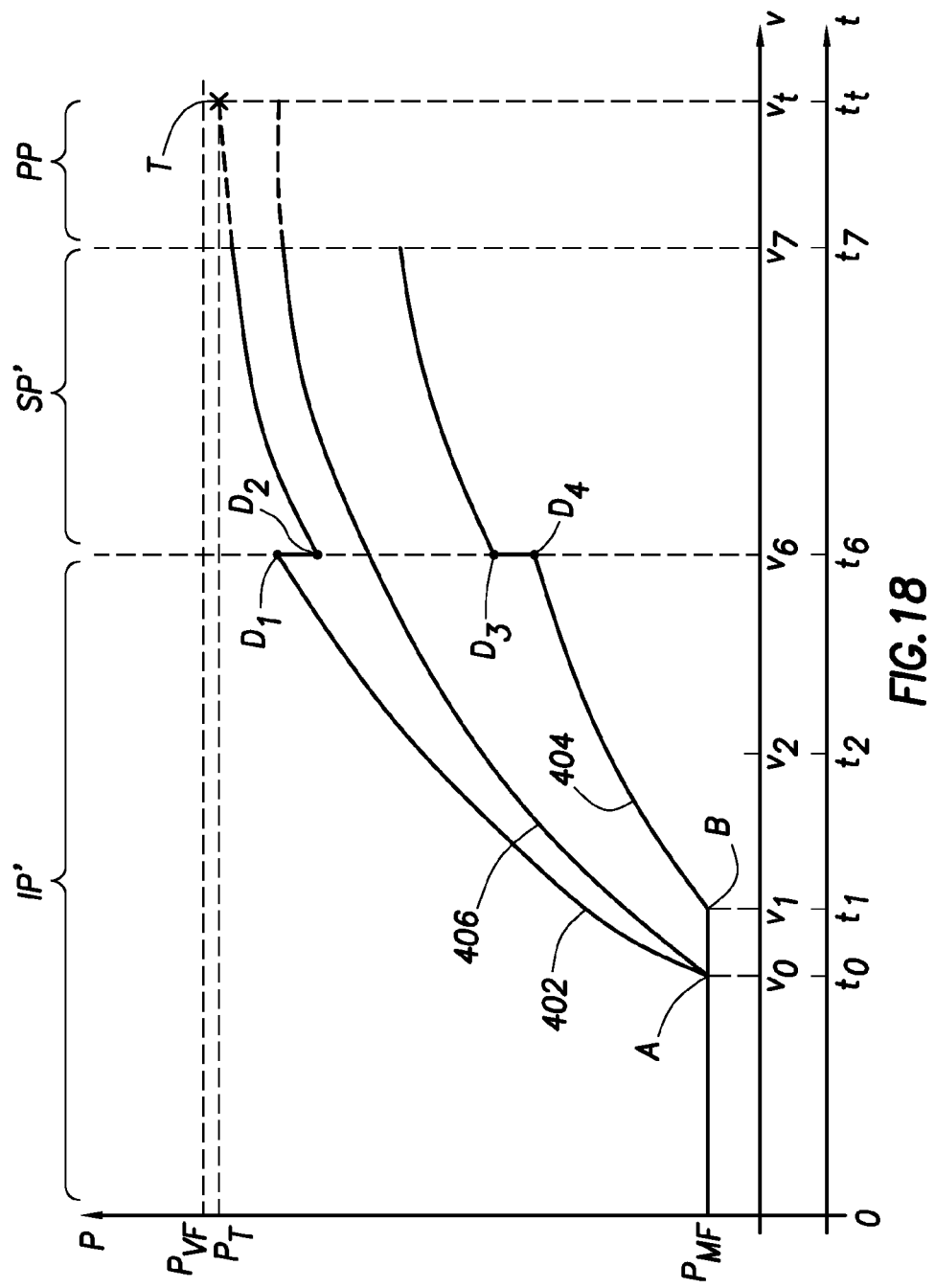
FIG. 18 is a graph of a fluid property of the flowlines of the fluid flow system of FIG. 14 using a time estimation technique.

FIG. 18 shows a graph of the relationship between a fluid property versus time and volume using a time estimation technique. In particular, FIG. 18 relates to the estimation of cleanup times generated using evaluation, merged and cleanup flowlines. The fluid may be drawn into the tool using the evaluation and/or cleanup flowlines as previously described with respect to FIG. 14.

Lines 402, 404 and 406 depict the fluid property levels for the evaluation, cleanup and merged flowlines, respectively. As described with respect to FIGS. 15A and 16, the fluid property for the evaluation and combined flowlines increases at point A after the virgin fluid breaks through. These lines continue to increase through an initial phase IP'. At time t6 and volume V6, the flow rates shift and the fluid property briefly lowers from point D1 to D2 in the evaluation flowline as flow into the evaluation flowline increases. A corresponding reduction in flow rate in the cleanup flowline causes the cleanup line 404 to shift from Points D3 to D4. The evaluation and cleanup flowlines then continue to increase through second phase SP'. In the example shown, no corresponding change is seen in the combined flowline and it continues to increase steadily into the second phase SP'. As described above with respect to FIGS. 15A and 16, the shift due to changes in flow rate may occur in a variety of ways or not at all.

In some cases, such as those shown in FIGS. 15A, 15B and 16, the fluid properties are known for a given time period. In some cases, the fluid property for one or more flowlines may not be known. The fluid properties and the corresponding line may be generated using the techniques described with respect to FIG. 16. Plots may be estimated for a into a future phase PP by projecting fluid property estimates beyond time t7 and volume V7.

It may be desirable to determine when the evaluation flowline reaches a target contamination level $P_T$. In order to determine this, the information known about the existing flowlines and their corresponding fluid properties P may be used to predict future parameter levels. For example, the merged flowline may be projected into a future projection phase PP.

The relationship between the merged and evaluation flowlines may then be used to extend a corresponding projection for line 402 into the projection phase PP using the techniques described with respect to FIG. 16. The point T at which the evaluation flowline meets a target parameter level that corresponds to a desired contamination level may then be determined. The time to reach point T may then be determined based on the graph.

The merged flowline parameter line 406 may be determined using the techniques described with respect to FIGS. 16 and 17. The merged flowline parameter line 406 may then be projected into the future beyond time t7 and into the projected phase PP. The evaluation line 402 may then be extended into the projected phase PP based on the projected merged flowline 406 and the relationship depicted in FIG. 19.

Figure 19:
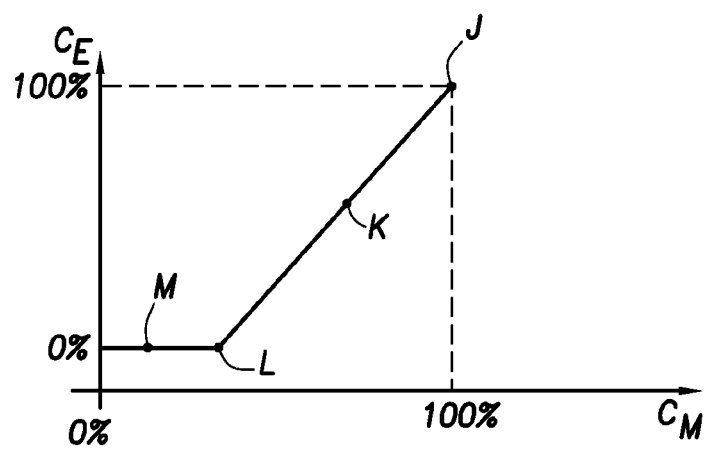
FIG. 19 is graph depicting the relationship between percent contamination for an evaluation flowline versus a combined flowline.

FIG. 19 shows a graph of an example of a relationship between the percent contamination of a combined flowline $C_M$ (x-axis) versus the percent contamination of an evaluation flowline $C_E$ (y-axis). The relationship of contamination in the flowlines may be determined empirically. At point J, fluid is initially drawn into the evaluation and combined flowline. Contamination level is at 100% since the no virgin fluid has broken through or is flowing into the tool. Once the virgin fluid breaks through, the contamination level begins to drop to point K. As cleanup continues, contamination levels continue to drop until fluid in the evaluation flowline is virgin at point L. Cleanup continues until the amount of contaminated fluid entering the cleanup flowline continues to reduce to point M.

The graph of FIG. 19 shows a relationship between the evaluation and combined flowline. This relationship may be determined using empirical data based on the relationship between flow rate in the evaluation flowline Qs and the flow rate in the evaluation flowline Qp. The relationship may also be determined based on rock properties, fluid properties, mud cake properties and/or previous sampling history, among others. From this relationship, the line 402 for the evaluation flowline may be projected based on the projected line 406 of the combined flowline. The point at which the projected evaluation line 402 reaches Target point occurs at time tT and volume Vt. This time tT is the time to reach the target cleanup.

The techniques described in relation to FIGS. 15A-19 can be practiced with any one of the fluid sampling systems described above. The various methods described for FIGS. 15A, 15B, 16 and 18 may be interchanged. For example, the calibration procedures described herein may be used in combination with any of these methods. Additionally, the method of projection and/or determining a time to reach a target contamination may be combined with the methods of FIGS. 15A, 15B and/or 16.

Figure 20:
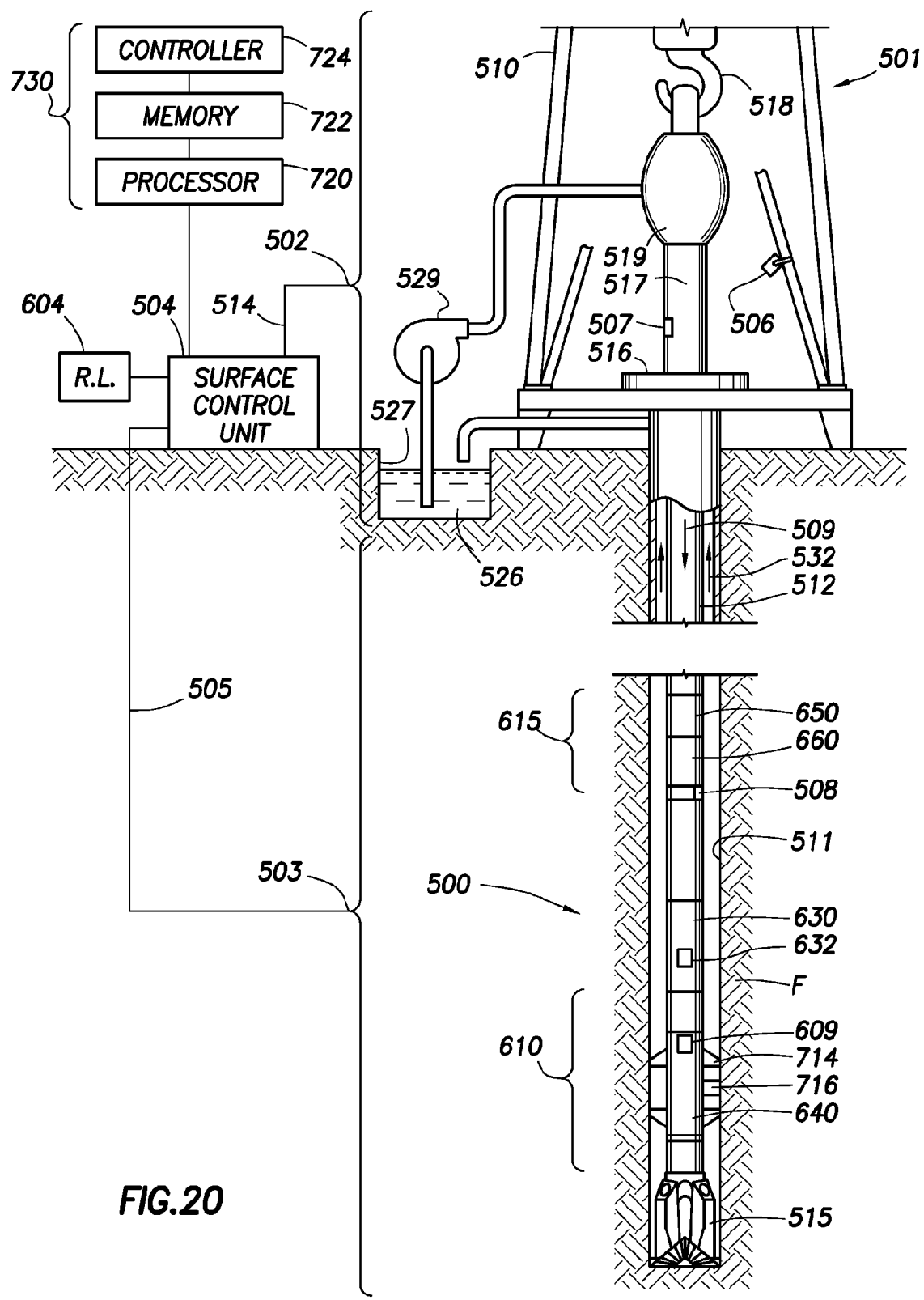
FIG. 20 is a schematic view of a wellsite having a rig with a downhole tool suspended therefrom and into a subterranean formation.

FIG. 20 illustrates a wellsite system 501 with which the present invention can be utilized to advantage. The wellsite system includes a surface system 502, a downhole system 503 and a surface control unit 504. In the illustrated embodiment, a borehole 511 is formed by rotary drilling in a manner that is well known. Those of ordinary skill in the art given the benefit of this disclosure will appreciate, however, that the present invention also finds application in other downhole applications other than conventional rotary drilling, and is not limited to land-based rigs. Examples of other downhole application may involve the use of wireline tools (see, e.g., FIG. 2 or 3), casing drilling, coiled tubing, and other downhole tools.

The downhole system 503 includes a drill string 512 suspended within the borehole 511 with a drill bit 515 at its lower end. The surface system 502 includes the land-based platform and derrick assembly 510 positioned over the borehole 511 penetrating a subsurface formation F. The assembly 510 includes a rotary table 516, kelly 517, hook 518 and rotary swivel 519. The drill string 512 is rotated by the rotary table 516, energized by means not shown, which engages the kelly 517 at the upper end of the drill string. The drill string 512 is suspended from a hook 518, attached to a traveling block (also not shown), through the kelly 517 and the rotary swivel 519 which permits rotation of the drill string relative to the hook.

The surface system further includes drilling fluid or mud 526 stored in a pit 527 formed at the well site. A pump 529 delivers the drilling fluid 526 to the interior of the drill string 512 via a port in the swivel 519, inducing the drilling fluid to flow downwardly through the drill string 512 as indicated by the directional arrow 509. The drilling fluid exits the drill string 512 via ports in the drill bit 515, and then circulates upwardly through the region between the outside of the drill string and the wall of the borehole, called the annulus, as indicated by the directional arrows 532. In this manner, the drilling fluid lubricates the drill bit 515 and carries formation cuttings up to the surface as it is returned to the pit 527 for recirculation.

The drill string 512 further includes a bottom hole assembly (BHA), generally referred to as 500, near the drill bit 515 (in other words, within several drill collar lengths from the drill bit). The bottom hole assembly includes capabilities for measuring, processing, and storing information, as well as communicating with the surface. The BHA 500 further includes drill collars 630, 640, 650 for performing various other measurement functions.

The BHA 500 includes the formation evaluation assembly 610 for determining and communicating one or more properties of the formation F surrounding borehole 511, such as formation resistivity (or conductivity), natural radiation, density (gamma ray or neutron), and pore pressure. The BHA also includes a telemetry assembly 615 for communicating with the surface unit 504. The telemetry assembly 615 includes drill collar 650 that houses a measurement-while-drilling (MWD) tool. The telemetry assembly further includes an apparatus 660 for generating electrical power to the downhole system. While a mud pulse system is depicted with a generator powered by the flow of the drilling fluid 526 that flows through the drill string 512 and the MWD drill collar 650, other telemetry, power and/or battery systems may be employed.

Formation evaluation assembly 610 includes drill collar 640 with stabilizers or ribs 714 and a probe 716 positioned in the stabilizer. The formation evaluation assembly is used to draw fluid into the tool for testing. The probe 716 may be similar to the probe as described in, e.g., FIG. 14. The flow circuitry and other features of FIG. 14 may also be provided in the formation evaluation assembly 610. The probe may be positioned in a stabilizer blade as described, for example, in U.S. Patent Application Publication No. 2005/0109538.

Sensors are located about the wellsite to collect data, preferably in real time, concerning the operation of the wellsite, as well as conditions at the wellsite. For example, monitors, such as cameras 506, may be provided to provide pictures of the operation. Surface sensors or gauges 507 are disposed about the surface systems to provide information about the surface unit, such as standpipe pressure, hook load, depth, surface torque, rotary rpm, among others. Downhole sensors or gauges 508 may be disposed about the drilling tool and/or wellbore to provide information about downhole conditions, such as wellbore pressure, weight on bit, torque on bit, direction, inclination, collar rpm, tool temperature, annular temperature and toolface, among others. Additional formation evaluation sensors 609 may be positioned in the formation evaluation sensors to measure downhole properties. Examples of such sensors are described with respect to FIG. 14. The information collected by the sensors and/or cameras is conveyed to the surface system, the downhole system and/or the surface control unit.

The telemetry assembly 615 uses mud pulse telemetry to communicate with the surface system. The MWD tool 650 of the telemetry assembly 615 may include, for example, a transmitter that generates a signal, such as an acoustic or electromagnetic signal, which is representative of the measured drilling parameters. The generated signal is received at the surface by transducers (not shown), that convert the received acoustical signals to electronic signals for further processing, storage, encryption and use according to conventional methods and systems. Communication between the downhole and surface systems is depicted as being mud pulse telemetry, such as the one described in U.S. Pat. No. 5,517,464. It will be appreciated by one of skill in the art that a variety of telemetry systems may be employed, such as wired drill pipe, electromagnetic or other known telemetry systems. It will be appreciated that when using other downhole tools, such as wireline tools, other telemetry systems, such as the wireline cable or electromagnetic telemetry, may be used.

The telemetry system provides a communication link 505 between the downhole system 503 and the surface control unit 504. An additional communication link 514 may be provided between the surface system 502 and the surface control unit 504. The downhole system 503 may also communicate with the surface system 502. The surface unit may communicate with the downhole system directly, or via the surface unit. The downhole system may also communicate with the surface unit directly, or via the surface system. Communications may also pass from the surface system to a remote location 604.

One or more surface, remote or wellsite systems may be present. Communications may be manipulated through each of these locations as necessary. The surface system may be located at or near a wellsite to provide an operator with information about wellsite conditions. The operator may be provided with a monitor that provides information concerning the wellsite operations. For example, the monitor may display graphical images concerning wellbore output.

The operator may be provided with a surface control system 730. The surface control system includes surface processor 720 to process the data, and a surface memory 722 to store the data. The operator may also be provided with a surface controller 724 to make changes to a wellsite setup to alter the wellsite operations. Based on the data received and/or an analysis of the data, the operator may manually make such adjustments. These adjustments may also be made at a remote location. In some cases, the adjustments may be made automatically.

Drill collar 630 may be provided with a downhole control assembly 632. The downhole control assembly includes a downhole processor for processing downhole data, and a downhole memory for storing the data. A downhole controller may also be provided to selectively activate various downhole tools. The downhole control assembly may be used to collect, store and analyze data received from various wellsite sensors. The downhole processor may send messages to the downhole controller to activate tools in response to data received. In this manner, the downhole operations may be automated to make adjustments in response to downhole data analysis. Such downhole controllers may also permit input and/or manual control of such adjustments by the surface and/or remote control unit. The downhole control system may work with or separate from one or more of the other control systems.

The wellsite setup includes tool configurations and operational settings. The tool configurations may include for example, the size of the tool housing, the type of bit, the size of the probe, the type of telemetry assembly, etc. Adjustments to the tool configurations may be made by replacing tool components, or adjusting the assembly of the tool.

For example, it may be possible to select tool configurations, such as a specific probe with a predefined diameter to meet the testing requirements. However, it may be necessary to replace the probe with a different diameter probe to perform as desired. If the probe is provided with adjustable features, it may be possible to adjust the diameter without replacing the probe.

Operational settings may also be adjusted to meet the needs of the wellsite operations. Operational settings may include tool settings, such as flow rates, rotational speeds, pressure settings, etc. Adjustments to the operational settings may typically be made by adjusting tool controls. For example, flow rates into the probe may be adjusted by altering the flow rate settings on pumps that drive flow through sampling and contamination flowlines (see, e.g., pumps 135*a*2, b of FIG. 14). Additionally, it may be possible to manipulate flow through the flowlines by selectively activating certain valves and/or diverters (see, e.g., diverter 148 and valves 144*a-d* of FIG. 14).

Figure 21:
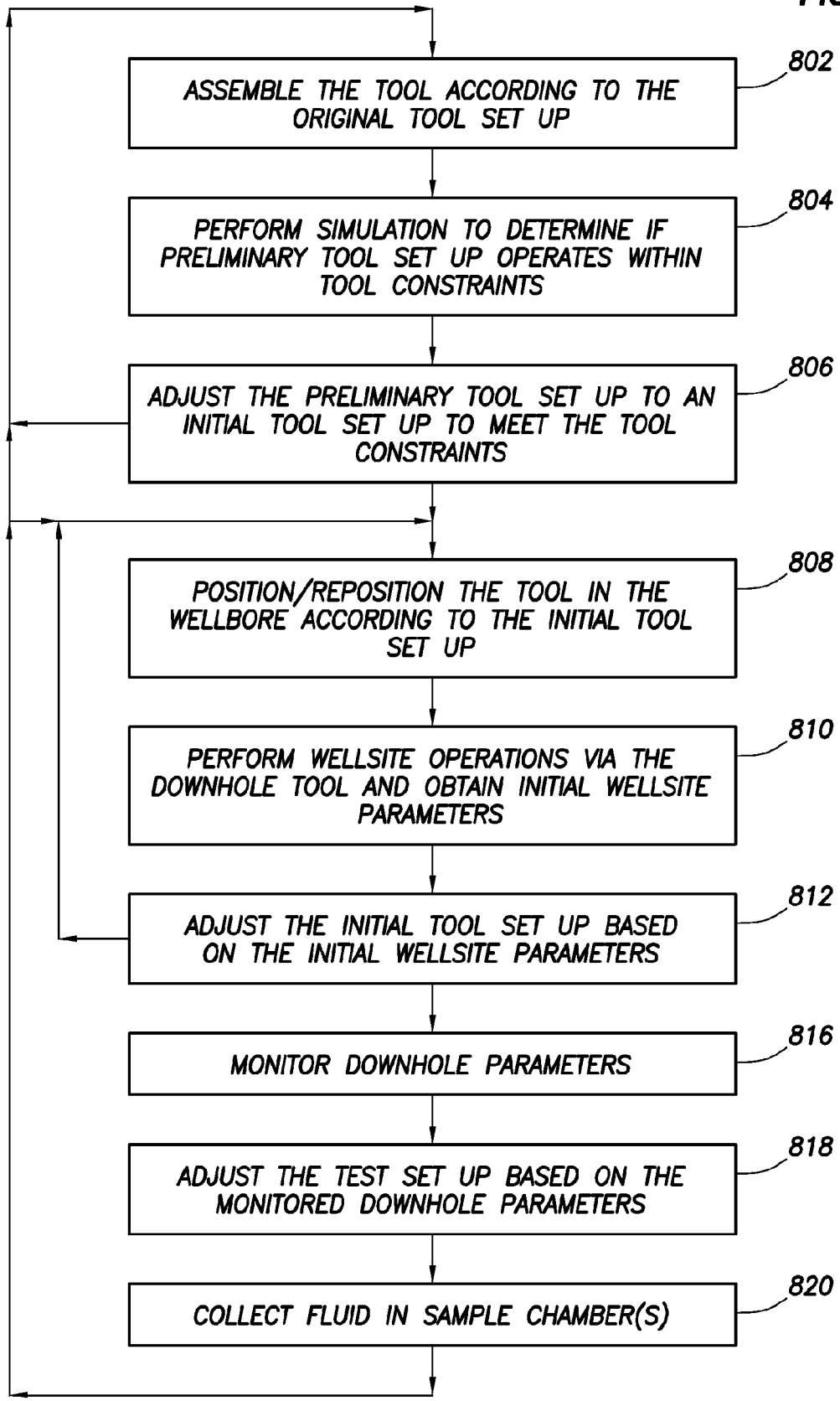
FIG. 21 is a flow chart depicting a method of evaluation a subterranean formation via a downhole tool according to a tool setup, the method involving adjustments to the tool set up.

FIG. 21 depicts a method of evaluating a formation. Steps 802, 804 and 806 relate to a preliminary tool set up. The preliminary tool set up is the tool set up used at the surface for tool assembly. The tool is initially assembled according to the preliminary tool setup 802. Typically, the tool is configured based on an estimate of the desired tool operation. For example, to drill an 8" diameter well, an 8" diameter bit is provided. The desired tools, such as an MWD telemetry tool, a probe for performing formation pressure while drilling tests and a set of sensors for measuring desired parameters, are also predefined and assembled in the tool.

Once the tool, or portions of the tool, are assembled, simulations may be run at the surface to determine if the tool will operate as desired 804. Certain tool constraints (or operating criteria) may be pre-defined. The tool may be required to perform within these constraints. If the tool fails to meet these constraints, adjustments to the preliminary tool set up may be made. The process may be repeated until the tool performs as desired. Once the necessary adjustments are made and the tool meets the tool constraints, an initial tool set up is defined for the tool 806.

The tool may then be sent downhole for use 808. The tool may be positioned in the well at one or more locations as desired. Typically, in drilling operations, the tool advances into the well as the tool is drilled. However, drilling and/or wireline tools may be repositioned throughout the well as desired to perform various operations.

As shown in block 810, the tool may be positioned to perform initial downhole tests. A variety of tests using a variety of components may be used. For example, sensors may be used to measure wellbore parameters, such as annular pressure. In other examples, resistivity tools may be positioned to take resistivity measurements. In yet another example, the formation evaluation assembly may be positioned and activated to draw fluid into the downhole tool for testing and/or sampling. Testing parameters may then be generated from these initial tests.

The initial test parameters may be collected by the downhole processor and analyzed. This information may be stored in memory and/or combined with other wellsite data, compared with pre-entered information and/or otherwise analyzed. The tool may be programmed to respond to certain data and/or data output. The surface and/or downhole controllers may then activate the tool in response to this information. In some cases, the information may indicate that the initial tool set up needs to be adjusted in response to the initial test parameters. It may be necessary to retrieve the tool to the surface and repeat steps 802-806 to adjust the initial tool setup. The process may be repeated until the tool operates as desired.

If an adjustment is necessary, the initial tool set up is adjusted to a target test set up that meets the requirements of the wellbore operations 812. For example, the testing parameters may indicate that a time for performing the testing is limited. The testing operation may then be defined to perform within the time constraints. In another example, flow rate through one or more inlets of the probe may be adjusted by adjusting pumping rates to reduce contamination levels.

Once the target test set up is established, it may be desirable to perform additional functions, such as sampling. Fluid may be drawing into the fluid and collected in a sample chamber. During this sampling process, the downhole parameters may be monitored 816. The target test set up may be adjusted as additional data is collected. The wellsite conditions may change, or more information may suggests that the target test set up should be further refined. Adjustments to the target test set up may be made and a refined target test set up may be defined based on the monitored downhole parameters 818. Fluid samples may be collected as desired 820.

A specific example applying the above method to the tool of FIG. 14 will now be presented. The preliminary tool set up may be defined to provide a downhole wireline tool with the configuration of FIG. 14. The probe is provided with a predefined diameter, and the tool is provided with the valving, sensors, pumps and sample chambers as depicted. A simulation of the tool is run, and it is determined that the probe diameter needs to be adjusted to provide the desired flow of fluid into the tool during formation evaluation of formation fluid. The preliminary tool set up is then adjusted to an initial tool setup to meet the formation evaluation requirements. The tool is then provided with a probe having the desired diameter.

The tool is then positioned downhole at a location determined by logs taken during drilling. The tool is activated so that the probe deploys against the wellbore for testing as shown in FIG. 14. The tool performs initial downhole tests according to the rates defined in the initial tool setup. During these tests, sensors (146*a, b*) indicate that contamination levels are high in both the sample and contamination flowlines (128, 130). To reduce the contamination levels, the pumping rates of pump 36*d* is increased to draw contamination into contamination flowline 130 and away from sampling flowline 128. This change is used to adjust the flow rate (initial tool set up) to an increased flow rate (target test set up) based on the sensor readings (initial downhole parameters). As a result, contamination levels in the sampling flowline are reduced.

The fluid parameters may be continuously monitored by the sensors as it flows through the flowlines. Once the fluid in the sampling flowline is considered virgin, the fluid may be collected in a sample chamber 142*a*. During the monitoring, it may be discovered that a problem, such as a lost seal or blocked flowline, has occurred. The target test setup may be adjusted to define a refined test setup based on the data. In some cases, the tool may have to be reset into position to start new tests. Alternatively, fluid may be merged, separated, diverted or otherwise manipulated to perform desired testing or to be dumped from the tool.

As needed, the tool may be retrieved for further adjustments. Various other tools, such as MWD tools, may be activated to perform additional tests. As desired, the tool may be programmed to make the necessary adjustments automatically using wellsite processors, such as downhole processor 632 and/or surface processor 722.

The operator (at the surface and/or remote location) may also be provided with surface displays which depict configurations of the wellsite operations. In one example, the operator may be provided with graphical depictions of contamination levels. As adjustments are made in response to contamination levels, the operator may visually see the shifts in operations. The operator may manually make additional adjustments to the tool set up to reach the desired operation levels. The operator may manually perform the adjustments, shift automatic adjustments or merely monitor automatic adjustments.

This example may also be used in a drilling operation. In cases where the formation evaluation tool is in a drilling tool, the initial tool set up may be defined such that tests are performed when the tool stops and/or terminate under certain conditions. The initial tool set up may also be defined to provide for time limited tests and/or pretest(s). During monitoring of target downhole parameters, it may be necessary to terminate the operation if the seal is lost and/or the drilling tool is activated. It may also be desirable to selectively activate telemetry systems to send data to the surface. The drilling operation may also be selectively reactivated to continue advancing the drilling tool into the earth to form the wellbore.

In the case of a downhole tool having a probe with a sampling intake and a contamination intake as depicted in FIG. 14, various downhole parameters may be of particular interest. For example, simulations may be used to map the regimes of focused sampling tool operation versus the reservoir fluid mobility under different constraints for total power available, rates of pumping out through sample and guard production systems, differential pressure across the inner packer at sand face, and etc. The adjustment of wellsite and/or tool setups may be used to tune the downhole tool in order to obtain high quality samples of formation fluid under reliable and safe tool operation. Preferably, such tuning may be performed in real time based on measured parameters.

Known data and/or modeled parameters may be used to provide procedures, rules and/or instructions that define the operating constraints necessary for safe and reliable wellsite operations. For example, hardware capabilities may be modeled and implemented to define wellsite setup relating to items, such as probes, power settings, displacement units, and pumps, Software may be configured to perform the simulations, such as focused sampling tool operation during pumping out. Software may also be configured to perform closed loop operation instructions relating to tool control, such as pumping out to sample recovery and tool retraction.

Figure 22A:
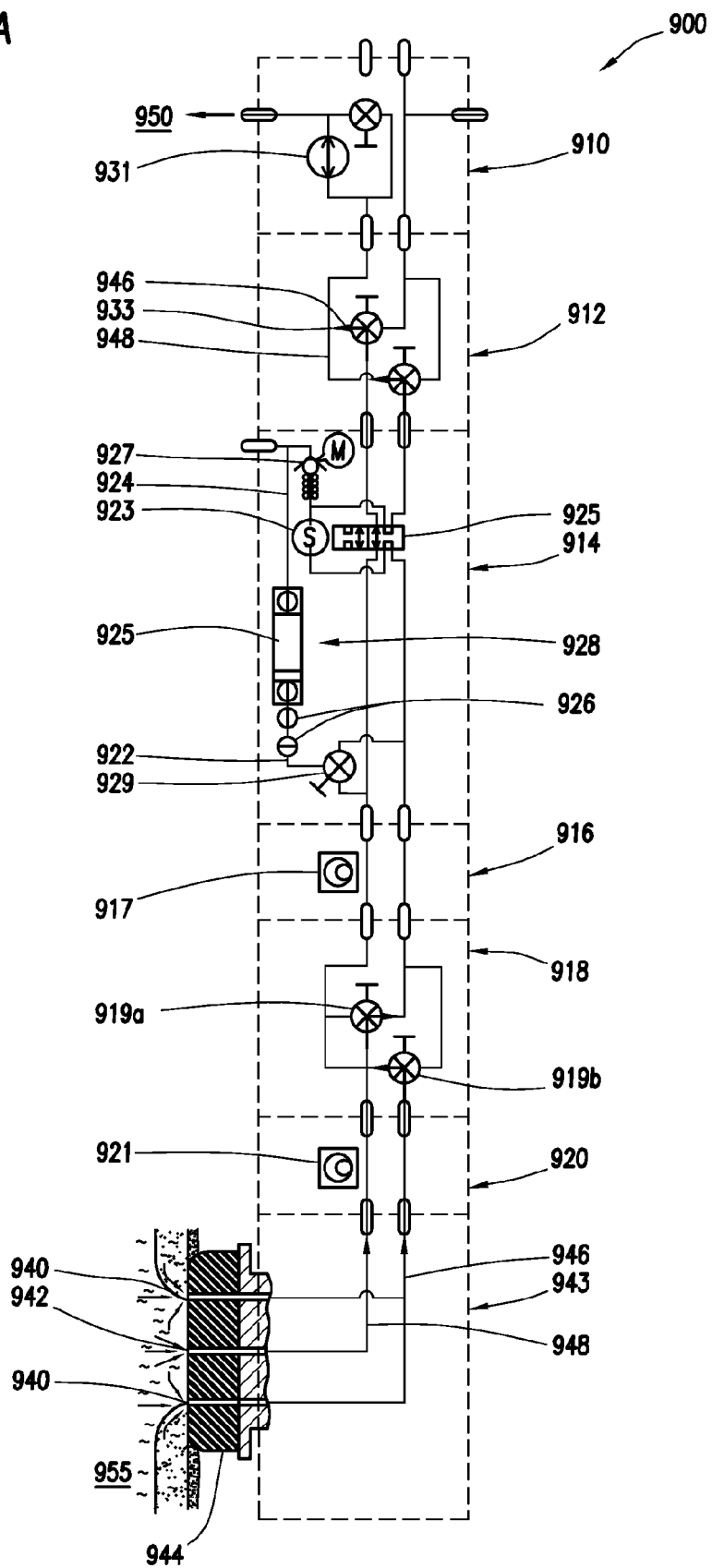
FIGS. 22A and 22B are schematic views of an apparatus according to one or more aspects of the present disclosure.
Figure 22B:
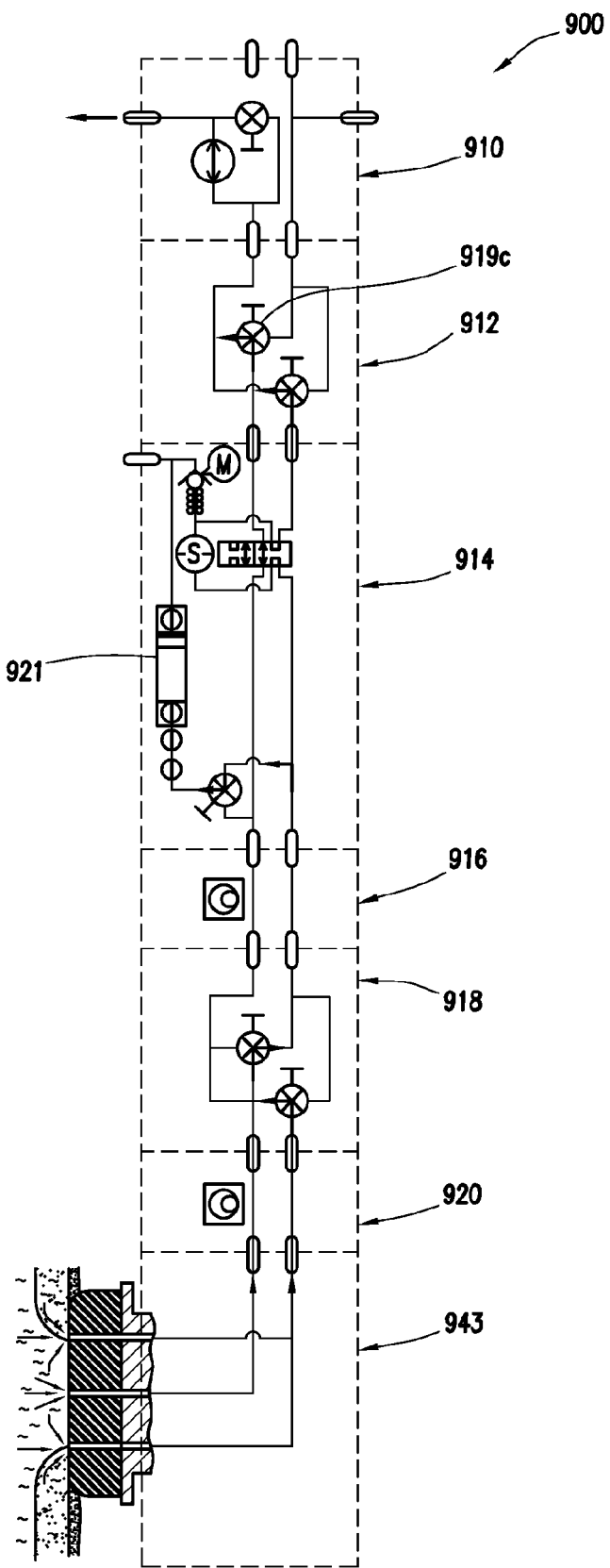

Referring to FIGS. 22A and 22B, illustrated is a schematic view of a downhole tool 900. The downhole tool 900 may be or comprise one or more aspects of the downhole tool 10, the fluid sampling system 26, and/or the probe 28 shown in FIGS. 3, 5 and/or 6A-6J. The downhole tool 900 may alternatively be or comprise one or more aspects of the tool 110 and/or the fluid flow system 134 shown in FIGS. 12, 13 and/or 14. In FIG. 22A, represented are the tool flow patterns during production cleanup. FIG. 22B illustrates the tool flow patterns during sample chamber fill-up.

The tool schematic shown in FIGS. 22A and 22B is one example of a simplified tool string configuration useful for downhole sampling, among other downhole operations. The tool schematic is shown with flow routing for focused sampling with a single pump module and merging evaluation and cleanup flowlines before the pump module. While the tool schematic shown in FIGS. 22A and 22B has less components than the existing focused sampling tool, such as a single pumpout versus two pumpout modules in existing focused sampling tool, the shown configuration may be attractive for the implementation of focused sampling functionality on drill pipe. It should be appreciated however that the tool schematic shown in FIGS. 22A and 22B may be implemented on any downhole tool performing formation evaluation services regardless of the conveyance means of such downhole tool without departing from the scope of the present disclosure. Thus, the tool schematic shown in FIGS. 22A and 22B may be used for obtaining clean reservoir fluid and gas during sampling applications using, for example, sampling systems on drill pipe (i.e., formation evaluation and/or reservoir sampling capabilities incorporated on a drill string), as well as wireline systems. Further, while the tool schematic shown is FIGS. 22A and 22B illustrates for clarity and/or simplicity a flow routing for focused sampling with a single pump module and merging evaluation and cleanup flowlines before the pump module, it should be apparent to those skilled in the art, given the benefit of the present disclosure, that three or more flowlines may be selectively merged into two or more pumps modules for performing focused sampling one a system having three or more inlets. Still further, the present disclosure also contemplates downhole tools for focused sampling with a plurality of pump modules, a plurality of flowlines in fluid communications with a corresponding one of a plurality of fluid intakes, and merging two or more of the plurality of flowlines before one of the plurality of pump modules (as shown, for example, in FIG. 14).

As shown in FIGS. 22A and 22B, a focused probe 944 is extended from the downhole tool 900 for engagement with the wellbore wall. The probe comprises one or more packers for sealing with the wellbore wall. The packer contacts the wellbore wall and forms a seal with the mudcake lining the wellbore. The probe 944 is provided with at least two intakes configured to receive fluid from the formation 955. The first intake may comprise a first flow channel 942, for example as discussed herein. The second intake may comprise a second flow channel 940 surrounding the first flow channel 942, such as shown for example in FIG. 6D. In cases where straddle packers are used (as shown in FIGS. 8A, 8B and/or 8C for example), a dual inlet for evaluation and cleanup may be incorporated into the tool instead of or in addition to the probe module 943.

The mud seeps through the wellbore wall and creates an invaded zone about the wellbore. The invaded zone contains mud and other wellbore fluids that contaminate the surrounding formations, including the formation 955 and a portion of the clean formation fluid contained therein.

The probe 944 is in fluid communication with at least two flowlines, including an evaluation flowline 948 and a cleanup flowline 946. The evaluation flowline 948 extends from the first intake into the downhole tool 900 and is used to pass clean formation fluid into the downhole tool 900 for testing and/or sampling. The cleanup flowline 946 extends from the second intake into the downhole tool 900 and is used to draw contaminated fluid away from the clean fluid flowing into the evaluation flowline 948. Contaminated fluid may be discharged in the wellbore 950.

The path of the evaluation flowline 948 and the cleanup flowline 946 in the downhole tool 900 may be adjusted using one or more routing modules, such as routing modules 912 and/or 918. In the configuration shown in FIGS. 22A and 22B, each routing module 912 or 918 comprises a fluid connector for passing fluid between flowlines fluidly connected to the routing module. For example, a fluid connector may comprise directional control valves, such as valves 919a and 919b, and connector flowlines. In the shown example, the directional control valves 919a and/or 919b may be implemented using two 3 ports-3 positions valves. A fluid connector may also be implemented in a way similar to the junction 151 and/or the cross-over 148 shown in FIG. 14.

In the configuration shown in FIGS. 22A and 22B, the fluid analyzer 921 (e.g., an optical fluid analyzer) in the fluid analysis module 920 is configured to measure a property of the fluid in the evaluation flowline 948, and is positioned close to the sand face (i.e., the interface between formation 955 and the probe 944). Depending on the job requirements, it may be more advantageous to measure the property of the fluid in the evaluation flowline 948 next to the sample carrier module 914, such as with the fluid analyzer 917 (e.g., an optical fluid analyzer) in the fluid analysis module 916. This may be exercised, for example, by switching the valves 919a and 919b in the lowermost routing module 918, and switching the valves 929 and 925 in the fluid sample carrier module 914.

As mentioned before, the schematic of the downhole tool 900 depicted in FIGS. 22A and 22B shows a single pump module 910 having one pump 931, and merging evaluation and cleanup flowlines at the merge point 933. Both evaluation and cleanup flowline fluids are separated or isolated in the downhole tool 900 until they merge at the merge point 933 in the uppermost routing module 912 just before the pump module 910. Thus, the pump 931 is configured to draw fluid from the formation 955 into the first and second intakes (e.g., the flow channels 942 and 940 respectively), and discharge at least a portion of the pumped fluid into the wellbore 950.

Fluid sample acquisition can be exercised using a sample carrier module 914 configured to acquire clean fluid samples 921 from the evaluation flowline 948. In a sampling technique according to one or more aspects of the present disclosure, the downhole tool 900 is configured for reverse low chock sampling. In the configuration shown, reverse low shock sampling is exercised with the fluid sample carrier module 914 placed between the probe module 943 and the pump module 910. The evaluation flowline 948 and the first intake (e.g., the flow channel 942) may fluidly communicate to a sample chamber 928 via the flowline 922 and the valve 929 for collecting samples 921 of formation fluid. A seal valve 923 is disposed on the evaluation flowline 948 between the first intake 942 of the probe 944 and the pump 931. The seal valve 923 is configured to selectively divert fluid drawn from the formation 955 and into the evaluation flowline 948 to the sample chamber 928. For example, the seal valve 923 is shown open in FIG. 22A (illustrating production cleanup) and close in FIG. 22B (illustrating sample chamber fill-up).

The sample chamber 928 is at least partially defined by a sliding piston configured to fluidly isolate the sample 921 from a cushion fluid 935 (e.g., water). The flowline 922 is selectively fluidly coupled to the first intake and the sample chamber 928 via the one-shot valves 926. The cushion fluid 935 (e.g., water) may be pumped through the flowline 924 and out of the back of the sample chamber 928 using the pump 931. By doing so, the sample 921 of formation fluid may be admitted into the sample chamber 928. In the shown configuration, a relief valve 927 isolates at least partially the flowline 924. For example, the relief valve 927 may be used to prevent flow in direction towards the flowline 924. Additionally, the relief valve 927 may be used to pressurize the flowline 924 with cushion fluid as some nominal pressure by which the cushion fluid may remain in the flowline 924 while the downhole tool 900 is conveyed in the wellbore 950.

For simplicity, only a single sample chamber 928 is shown in FIGS. 22A and 22B. In some cases, multiple sample chambers (bottles) are available for the sample carrier module. Also, FIGS. 22A and 22B show the function of the routing module 912 as an independent module. However, its function may also or alternatively be integrated into one of the other modules in the tool 900.

During production cleanup, there should be no issue with prematurely pulling the cushion fluid 935 out of the back of the sample chamber 928 even while a single pump module and merging flowlines. One of the valves 926 below the sample chamber is closed during production cleanup. Thus, the cushion fluid will stay in the back of sample chamber 928 until a first one of the valves 926 is opened.

However, it may be important to insure the pressure in the cleanup and evaluation flowlines are balanced or equalized appropriately during sample chamber fill-up operations. In the configuration shown, the management of the differential pressure between cleanup and evaluation flow lines during sample chamber fill-up is exercised using a pilot relief valve 927 of suitable characteristics that is disposed on the flowline 924 in the sample carrier module 914, between the back of the sample chamber 928 and the pump 931. Special attention may be required when defining the characteristics of the relief valve 927, as well as operating the relief valve 927 when performing focused sampling with merging flowlines and one pump module. For example, if the cracking pressure of the relief valve 927 is too low and/or if the relief valve 927 is omitted or bypassed, the fluid pressure at the second intake of the probe 944 may exceed the fluid pressure at the first intake of the probe 944, for example when the hydraulic resistance in the cleanup flowline is lower than the hydraulic resistance cleanup flowline. In these cases, one could acquire contaminated fluid in the evaluation flowline 948 and/or in the sample chamber 928. Conversely, if the cracking pressure of the relief valve 927 is too high, one may not be able to acquire fluid in the evaluation flowline 948 and/or in the sample chamber 928. Obviously, it would thus be advantageous if the functionality or characteristics of the relief valve 927 may be modified based on differential fluid pressure between the first and second intakes and/or fluid flow rate through one or more of the first and second intakes. The capability of modifying the functionality or characteristics of the relief valve 927 may facilitate unconditional acquisition of clean formation fluid samples.

One method of modifying the functionality or characteristics of the relief valve 927 is to selectively bypass or disconnect the relief valve 927. A simple downhole controllable device may force the relief valve open and allow the pressure relief function of the valve to be selectively reduced or suppressed (i.e., reduce or suppress the pressure drop generated across the valve). In closed position, the relief valve functions normally based on its cracking pressure. When the relief valve is forced in open position, fluid in the back of the sample chamber 928 may flow essentially freely through the flowline 924. For example, FIGS. 22A-22B show a symbolic representation of the pilot relief valve 927 including a bypass mechanism actuated by a motor M. The motor M may be an electric motor. The motor M actuates and mechanically pilots (i.e., opens) the relief valve in the fluid sample carrier 914.

Another important benefit of the tool configuration with merging flowlines using a single pump shown in FIGS. 22A-22B is the ability to over-pressure the acquired fluid sample 921. Over-pressuring the sample may be used to reduce the risk of the sample reaching a phase transition point (e.g., a bubble point) as the downhole tool 900 is pulled up to the Earth's surface.

Over-pressuring the fluid sample 921 can be exercised, for example, once the sample 921 has been captured in the sample chamber 928 by closing the second one of the one-shot valves 926. The technique may involve switching the valve 919c on the cleanup flowline 946 in the top most routing module 912, for example by actuating a downhole switch. This will isolate the cleanup flowline 946 from the pump 931. Once this is done, the flow generated by the pump 931 is reversed, while keeping the seal valve 923 in the sample carrier module 914 in the closed position, and while placing the mechanically piloted relief valve 927 in the open position. Thus, the acquired fluid sample 921 may be over-pressurized by pumping against the back side of the sample chamber 928. After this, the mechanically piloted relief valve 927 is placed in the closed position before the downhole tool 900 is pulled up to the Earth's surface. After pulling out of the hole, the sample chamber 928 will likely be at the cracking pressure of the relief valve 927. Therefore, this over-pressuring technique may call for various pressure relief valves depending on the operation parameters (such as the sampling depth)—or alternatively a downhole adjustable relief valve. Before anything is removed, the manual valves on the sample chamber 928 are closed. Once this is done, the fluids in the sample chamber 928 are held under pressure and the chamber can be removed from the sample carrier module 914.

One disadvantage of this over-pressuring technique may be the reduction of the volume of compressible fluid samples such as gas condensate samples. It may however be acceptable to reduce the sample volume slightly in order to over-pressurize the sample. This technique is unique compared to traditional techniques currently used for over-pressurizing fluid samples. There will be two fluid samples contained in each sample chamber. A first fluid sample is stored during the focused sample operation, and is contained, under pressure, on the front side of the sample chamber 928. The second fluid (e.g., cushion fluid contaminated with borehole fluid) is stored during the over-pressurizing operations, and is contained, under pressure, on the back side of the sample chamber 928.

Over-pressuring the fluid sample 921 can also be exercised, before the front side of the sample chamber 928 is isolated from the flowline 922 by closing the second one of the one-shot valve 926. This alternate technique may involve switching the valve 919c on the cleanup flowline 946 in the top most routing module 912, as previously discussed, and closing the valves 919a and 919b. Closing the valves 919a and 919b will isolate both flowlines towards the sample carrier module 914 above the routing module 918 from both flowlines towards the focused probe module 943 below the routing module 918. Isolating said flow lines permits not to over-pressurize the packer in the probe 944, and/or not to apply pressure to the formation 955. Once the foregoing valve switching is done, the seal valve 923 in the sample carrier module 914 is opened, the mechanically piloted relief valve 927 is placed in the close position and the flow generated by the pump 931 is reversed. Thus, the acquired fluid sample 921 is over-pressurized by pumping against the front side of sample chamber 928. After over-pressuring the sample, the sample chamber is isolated from the flowline 922 by closing the second one of the one-shot valve 926, capturing thereby the over-pressurized fluid 921, and the downhole tool 900 is pulled up to the Earth's surface.

One requirement of this alternative over-pressuring technique may be that both routing modules 912 and 918 utilize downhole switch-able valves.

Figure 23:
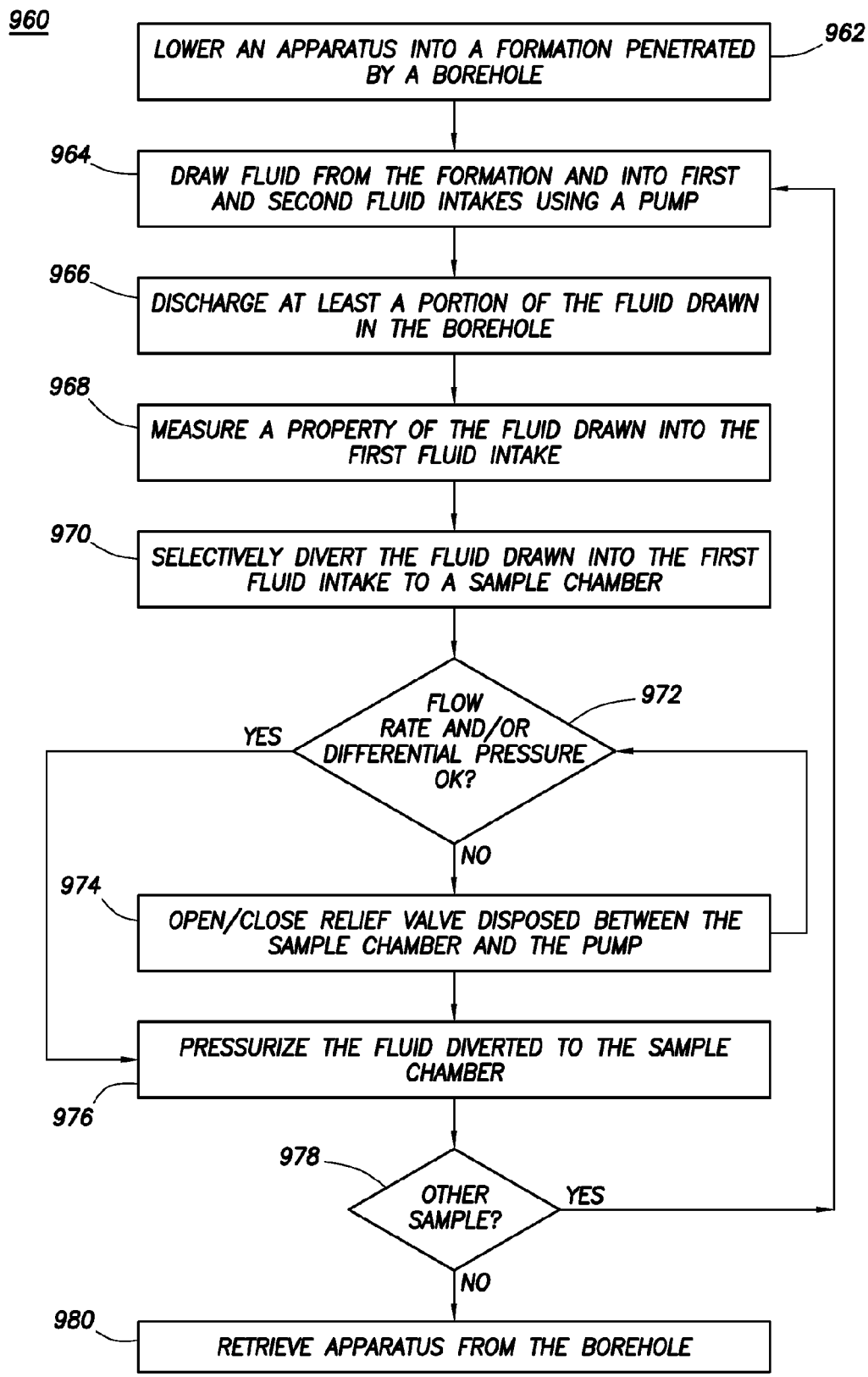
FIG. 23 is a flow-chart diagram of at least a portion of a method according to one or more aspects of the present disclosure.

FIG. 23 is a flow-chart diagram of a method 960 of focused sampling of subterranean formation fluid with a single pump module and merging evaluation and cleanup flowlines before the pump module. It should be appreciated that the order of execution of the steps depicted in the flow chart of FIG. 23 may be changed and/or some of the steps described may be combined, divided, rearranged, omitted, eliminated and/or implemented in other ways within the scope of the present disclosure.

At step 962, a sampling apparatus may be lowered into a subterranean formation penetrated by a borehole. Lowering the sampling apparatus may be performed using at least one of a drill string and a wireline, among other means of conveyance of the sampling apparatus in the borehole. The sampling apparatus may comprise first and second fluid intakes, a pump, and a sample chamber. For example, the sampling apparatus may be of a type similar to the downhole tool 10, the fluid sampling system 26, and/or the probe 28 shown in FIGS. 3, 5 and/or 6A-6J. The sampling apparatus may also be of a type similar to the downhole tool 900 shown in FIGS. 22A and 22B. However, other sampling apparatuses may be lowered into the formation at step 962 within the scope of the present disclosure.

At step 964, fluid may be drawn from the subterranean formation and into the first and second intakes using the pump of the sampling apparatus. For example, the first intake may be fluidly coupled to an evaluation flowline of the sampling apparatus (e.g., the flowline 38 shown in FIG. 5 and/or the flowline 948 shown in FIGS. 22A-22B). The second intake may be fluidly coupled to a cleanup flowline of the sampling apparatus (e.g., the flowline 40 shown in FIG. 5 and/or the flowline 946 shown in FIGS. 22A-22B). The evaluation flowline and the cleanup flowline may be merged at a merge point before the pump (e.g., the pump 35 shown in FIG. 5 and/or the pump 931 shown in FIGS. 22A-22B). Thus, as previously discussed herein, actuating the pump may draw clean or virgin fluid from the subterranean formation into the first intake, and contaminated fluid into the second intake.

At step 966, at least a portion of the fluid drawn from the formation and into the second fluid intake may be discharged in the borehole. For example, fluid drawn from the formation and present in the pump may be discharged into the borehole. The fluid present in the pump comprises fluid drawn into the second fluid intake regardless whether the sampling operation is in a production cleanup or a sample chamber fill-up phase. Note however that the fluid present in the pump may also comprise fluid drawn into the first fluid intake during the production cleanup phase (and cushion fluid during sample chamber fill-up phase).

At step 968, a property of the fluid drawn from the formation and into the first intake may be measured. For example, an optical density may be monitored using the optical fluid analyzer 74 shown in FIG. 9 and/or the fluid analyzer 921 shown in FIGS. 22A-22B. Measuring the property at step 968 may be performed until an acceptable contamination level of the fluid drawn into the first fluid intake is observed, for example using techniques described previously herein.

At step 970, at least a portion of the fluid drawn from the formation and into the first fluid intake may be selectively diverted to the sample chamber of the sampling apparatus (e.g., the sample chamber 42 shown in FIG. 5 and/or the sample chamber 928 shown in FIGS. 22A-22B). For example, a valve (e.g., the valve 44 shown in FIG. 5 and/or the seal valve 923 shown in FIGS. 22A-22B) disposed on the evaluation flowline between the first fluid intake and the pump may be actuated to divert fluid to the sample chamber.

At step 972, a measurement indicative of a flow rate through at least one of the first and the second intakes may be performed. A measurement indicative of a pressure differential between the evaluation flow line and the cleanup flow line proximate the focused probe and/or the first and second intakes may also be performed.

As mentioned before in the description of FIGS. 22A-22B, if the cracking pressure of the relief valve 927 is too high, one may not be able to flow fluid in the evaluation flowline 948 and/or in the sample chamber 928 when the pump 931 is actuated, because fluid may only flow in the cleanup flowline. Thus, the flow rate measurement performed at step 972 may indicate an undesired too low flow rate towards the sample chamber, Conversely, if the relief valve 927 is bypassed, the fluid pressure at the second intake of the probe 944 may exceed the fluid pressure at the first intake of the probe 944. In these cases, one could acquire contaminated fluid in the evaluation flowline 948 and/or in the sample chamber 928. Thus, the differential pressure measurement performed at step 972 may indicate an undesired pressure balance between the evaluation and cleanup flowlines.

At step 974, a pilot relief valve (e.g., the pilot relief valve 927 shown in FIGS. 22A-22B) disposed on a flowline between a back of the sample chamber and the pump of the sampling apparatus may be actuated based on the measurements performed at step 972. For example, the pilot relief valve may be opened if the flow rate towards the sample chamber is deemed too low. The pilot relief valve may also be closed if the pressure in the cleanup flowline deemed to excessively exceed the pressure in the evaluation flowline. It should be noted that in the cases where the sampling apparatus comprises a plurality of pilot relief valves disposed in series on the flowline between the back of the sample chamber and the pump, one or more of the plurality of pilot relief valves may be actuated at step 974 based on the measurements performed at step 972 to achieve suitable flow rates and/or suitable pressure balance in the cleanup and evaluation flowlines.

The operations of step 972 and/or 974 may be repeated until the sample admitted in the sample chamber has reached a suitable volume. Then, at step 976, the fluid diverted in the sample chamber may be pressurized above at least one of a subterranean formation pressure and a borehole pressure. For example, over-pressuring techniques described in FIGS. 22A-22B may be used to perform the step 976.

The method 960 contemplates optionally capturing a plurality of formation fluid sample, in a plurality of sample chambers as indicated by step 978. The samples, optionally over-pressurized, may be used or analyzed (not shown) once the sampling apparatus is retrieved from the borehole at step 980.

In view of all of the above and FIGS. 1 to 4, it should be readily apparent to those skilled in the art that the present disclosure provides an apparatus, comprising first and second intakes configured to receive formation fluid from a subterranean formation penetrated by a borehole, a pump configured to draw formation fluid into the first and second intakes and discharge into the borehole at least a portion of the formation fluid drawn into the second intake, and a sample chamber in selective fluid communication with the first intake. The apparatus may further comprise a fluid connector configured to selectively establish a fluid connection between at least one of the first and second intakes and the pump. The first intake may comprise a first flow channel; and the second intake may comprise a second flow channel surrounding the first flow channel. The apparatus may further comprise a flow line in fluid communication with the first intake and the pump, and a valve disposed on the flow line between the first intake and the pump, and configured to selectively divert formation fluid drawn into the flow line to the sample chamber. The apparatus may further comprise a fluid analyzer configured to measure a property of a formation fluid drawn into the flow line. The fluid analyzer may comprise an optical fluid analyzer. The flow line may be a first flow line, and the apparatus may further comprise a second flow line in fluid communication with the second intake and the pump. The second flow line may further be in fluid communication with the first flow line at a merge point. The apparatus may further comprise a first flow line in fluid communication with the first intake and with the sample chamber, and a second flow line in fluid communication with a back side of the sample chamber and with the pump. The apparatus may further comprise a pilot relief valve disposed on the second flow line between the back side of the sample chamber and the pump. The pump may be configured to pressurize the sample chamber by pumping a fluid through the pilot relief valve.

The present disclosure also provides a method, comprising positioning an apparatus in a borehole penetrating a subterranean formation, the apparatus comprising first and second fluid intakes, a pump, and a sample chamber, drawing formation fluid from the subterranean formation and into the first and second fluid intakes using the pump, discharging into the borehole at least a portion of the formation fluid drawn into the second fluid intake, and selectively diverting at least a portion of the formation fluid drawn into the first fluid intake to the sample chamber. Selectively diverting the at least portion the formation fluid drawn into the first intake to the sample chamber comprises actuating a valve disposed on a flow line between the first fluid intake and the pump. The method may further comprise measuring a property of the formation fluid drawn into the first fluid intake. Measuring the formation fluid property may comprise measuring an optical density. The method may further comprise actuating a pilot relief valve disposed on a flow line between a back of the sample chamber and the pump. Actuating the pilot relief valve may be performed based on a measurement indicative of a differential pressure between a first flow line that is fluidly coupled to the first fluid intake, and a second flow line fluidly that is coupled to the second fluid intake. Actuating the pilot relief valve may be performed based on a measurement indicative of a flow rate through at least one of the first and second fluid intakes. The method may further comprise pressurizing the at least portion of the formation fluid diverted to the sample chamber above at least one of a subterranean formation pressure and a borehole pressure. Positioning the apparatus in the borehole penetrating the subterranean formation may be performed using at least one of a drill string and a wireline.

It will be understood from the foregoing description that various modifications and changes may be made in the preferred and alternative embodiments of the present invention without departing from its true spirit. The devices included herein may be manually and/or automatically activated to perform the desired operation. The activation may be performed as desired and/or based on data generated, conditions detected and/or analysis of results from downhole operations.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

It should also be understood that the discussion and various examples of methods and techniques described above need not include all of the details or features described above. Further, neither the methods described above, nor any methods which may fall within the scope of any of the appended claims, need be performed in any particular order. The methods of the present invention do not require use of the particular embodiments shown and described in the present specification, such as, for example, the exemplary probe 28 of FIG. 5, but are equally applicable with any other suitable structure, form and configuration of components.

Preferred embodiments of the present invention are thus well adapted to carry out one or more of the objects of the invention. Further, the apparatus and methods of the present invention offer advantages over the prior art and additional capabilities, functions, methods, uses and applications that have not been specifically addressed herein but are, or will become, apparent from the description herein, the appended drawings and claims.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An apparatus, comprising:
    first and second intakes configured to receive formation fluid from a subterranean formation penetrated by a borehole;
    a pump configured to:
    draw formation fluid into the first and second intakes; and
    discharge into the borehole at least a portion of the formation fluid drawn into the second intake;
    a sample chamber in selective fluid communication with the first intake; and
    a pilot relief valve coupled to the pump and the sample chamber via a second flow line, wherein the pilot relief valve comprises a bypass mechanism actuated by a motor.

2. The apparatus of claim 1 further comprising a fluid connector configured to selectively establish a fluid connection between at least one of the first and second intakes and the pump.

3. The apparatus of claim 1 wherein:
    the first intake comprises a first flow channel; and
    the second intake comprises a second flow channel surrounding the first flow channel.

4. The apparatus of claim 1 further comprising:
    a flow line in fluid communication with the first intake and the pump; and
    a valve disposed on the flow line between the first intake and the pump and configured to selectively divert formation fluid drawn into the flow line to the sample chamber.

5. The apparatus of claim 4 wherein the flow line is a first flow line, and further comprising a second flow line in fluid communication with the second intake and the pump.

6. The apparatus of claim 5 wherein the second flow line is further in fluid communication with the first flow line at a merge point.

7. The apparatus of claim 4 further comprising a fluid analyzer configured to measure a property of formation fluid drawn into the flow line.

8. The apparatus of claim 7 wherein the fluid analyzer comprises an optical fluid analyzer.

9. The apparatus of claim 1 further comprising:
    a first flow line in fluid communication with the first intake and with the sample chamber; and wherein
    the second flow line is in fluid communication with a back side of the sample chamber and with the pump.

10. The apparatus of claim 9 wherein the pilot relief valve is disposed on the second flow line between the back side of the sample chamber and the pump.

11. The apparatus of claim 10 wherein the pump is configured to pressurize the sample chamber by pumping a fluid through the pilot relief valve.

12. The apparatus of claim 1, wherein the pilot relief valve is configured to at least partially isolate the second flow line.

13. The apparatus of claim 1, wherein the pilot relief valve is configured to block flow towards the sample chamber.

14. The apparatus of claim 1, wherein pilot relief valve is configured to be forced into an open position.

15. The apparatus of claim 1, wherein the motor comprises an electric motor.

16. An apparatus, comprising:
    first and second intakes configured to receive formation fluid from a subterranean formation penetrated by a borehole;
    a pump configured to:
    draw formation fluid into the first and second intakes; and
    discharge into the borehole at least a portion of the formation fluid drawn into the second intake;
    a sample chamber in selective fluid communication with the first intake; and
    a pilot relief valve coupled to the pump and the sample chamber via a second flow line, wherein the pilot relief valve comprises a mechanically piloted relief valve configured to be mechanically actuated between an open position and a closed position.

17. The apparatus of claim 16, comprising a sensor configured to indicate a flow rate or pressure of formation fluid flowing through at least one of the first and second intakes, wherein the mechanically piloted relief valve is actuated between the open and closed positions based on the flow rate or pressure of formation fluid flowing through at least one of the first and second intakes.

18. The apparatus of claim 16 further comprising a fluid connector configured to selectively establish a fluid connection between at least one of the first and second intakes and the pump.

19. The apparatus of claim 16 wherein:
the first intake comprises a first flow channel; and
the second intake comprises a second flow channel surrounding the first flow channel.

20. The apparatus of claim 16 further comprising:
a flow line in fluid communication with the first intake and the pump; and
a valve disposed on the flow line between the first intake and the pump and configured to selectively divert formation fluid drawn into the flow line to the sample chamber.

* * * * *